United States Patent
Stevenson et al.

(10) Patent No.: US 8,483,840 B2
(45) Date of Patent: *Jul. 9, 2013

(54) DUAL FUNCTION TUNED L-C INPUT TRAP PASSIVE EMI FILTER COMPONENT NETWORK FOR AN ACTIVE IMPLANTABLE MEDICAL DEVICE

(75) Inventors: Robert A. Stevenson, Canyon Country, CA (US); Warren S. Dabney, Orchard Park, NY (US); Robert Shawn Johnson, North Tonawanda, NY (US); Scott W. Kelley, Woodland Hills, CA (US)

(73) Assignee: Greatbatch Ltd., Clarence, NY (US)

( * ) Notice: Subject to any disclaimer, the term of this patent is extended or adjusted under 35 U.S.C. 154(b) by 326 days.

This patent is subject to a terminal disclaimer.

(21) Appl. No.: 12/891,587

(22) Filed: Sep. 27, 2010

(65) Prior Publication Data

US 2011/0043297 A1    Feb. 24, 2011

Related U.S. Application Data

(63) Continuation-in-part of application No. 12/751,711, filed on Mar. 31, 2010, now Pat. No. 8,219,208, which is a continuation-in-part of application No. 12/489,921, filed on Jun. 23, 2009, now Pat. No. 7,751,903, application No. 12/891,587, which is a continuation-in-part of application No. 12/686,137, filed on Jan. 12, 2010, application No. 12/891,587, which is a continuation-in-part of application No. 12/407,402, filed on Mar. 19, 2009, now Pat. No. 8,195,295.

(60) Provisional application No. 61/144,102, filed on Jan. 12, 2009, provisional application No. 61/149,833, filed on Feb. 4, 2009, provisional application No. 61/150,061, filed on Feb. 5, 2009, provisional application No. 61/116,094, filed on Nov. 19, 2008, provisional application No. 61/038,382, filed on Mar. 20, 2008.

(51) Int. Cl.
*A61N 1/08* (2006.01)

(52) U.S. Cl.
USPC .............................................. 607/63; 607/60

(58) Field of Classification Search
USPC .................................. 607/36, 41, 60, 63, 116
See application file for complete search history.

(56) References Cited

U.S. PATENT DOCUMENTS

| | | | |
|---|---|---|---|
| 5,217,010 A | 6/1993 | Tsitlik et al. |
| 5,895,980 A | 4/1999 | Thompson |
| 6,424,234 B1 | 7/2002 | Stevenson |
| 6,529,103 B1 | 3/2003 | Brendel et al. |
| 6,999,818 B2 | 2/2006 | Stevenson et al. |
| 7,013,180 B2 | 3/2006 | Villaseca et al. |
| 7,038,900 B2 | 5/2006 | Stevenson et al. |
| 7,199,995 B2 | 4/2007 | Stevenson |

(Continued)

*Primary Examiner* — Carl H Layno
*Assistant Examiner* — Jon Eric C Morales
(74) *Attorney, Agent, or Firm* — Michael F. Scalise

(57) ABSTRACT

Decoupling circuits are provided which transfer energy induced from an MRI pulsed RF field to the housing for an active implantable medical device (AIMD) which serves as an energy dissipating surface. A novel L-C input trap filter is provided which has a dual function. The L-C trap acts as a broadband low pass EMI filter while at the same time also acts as an L-C trap in order to divert induced RF energy from the lead to the housing of the AIMD.

37 Claims, 16 Drawing Sheets

U.S. PATENT DOCUMENTS

| | | |
|---|---|---|
| 7,310,216 B2 | 12/2007 | Stevenson et al. |
| 7,489,495 B2 | 2/2009 | Stevenson |
| 7,620,453 B1 | 11/2009 | Propato et al. |
| 7,689,288 B2 * | 3/2010 | Stevenson et al. .............. 607/63 |
| 7,765,005 B2 | 7/2010 | Stevenson |
| 2005/0007718 A1 * | 1/2005 | Stevenson et al. ............ 361/118 |
| 2005/0113874 A1 | 5/2005 | Connelly et al. |
| 2005/0113876 A1 * | 5/2005 | Weiner et al. ................... 607/36 |
| 2005/0222642 A1 | 10/2005 | Przybyszewski et al. |
| 2007/0083244 A1 | 4/2007 | Stevenson et al. |
| 2007/0123949 A1 | 5/2007 | Dabney et al. |
| 2007/0203530 A1 | 8/2007 | Hubing et al. |
| 2009/0243756 A1 | 10/2009 | Stevenson et al. |
| 2010/0016936 A1 * | 1/2010 | Stevenson et al. ............ 607/116 |
| 2010/0023000 A1 | 1/2010 | Stevenson et al. |
| 2010/0217262 A1 * | 8/2010 | Stevenson et al. .............. 606/41 |
| 2010/0280584 A1 * | 11/2010 | Johnson et al. ............... 607/116 |

* cited by examiner

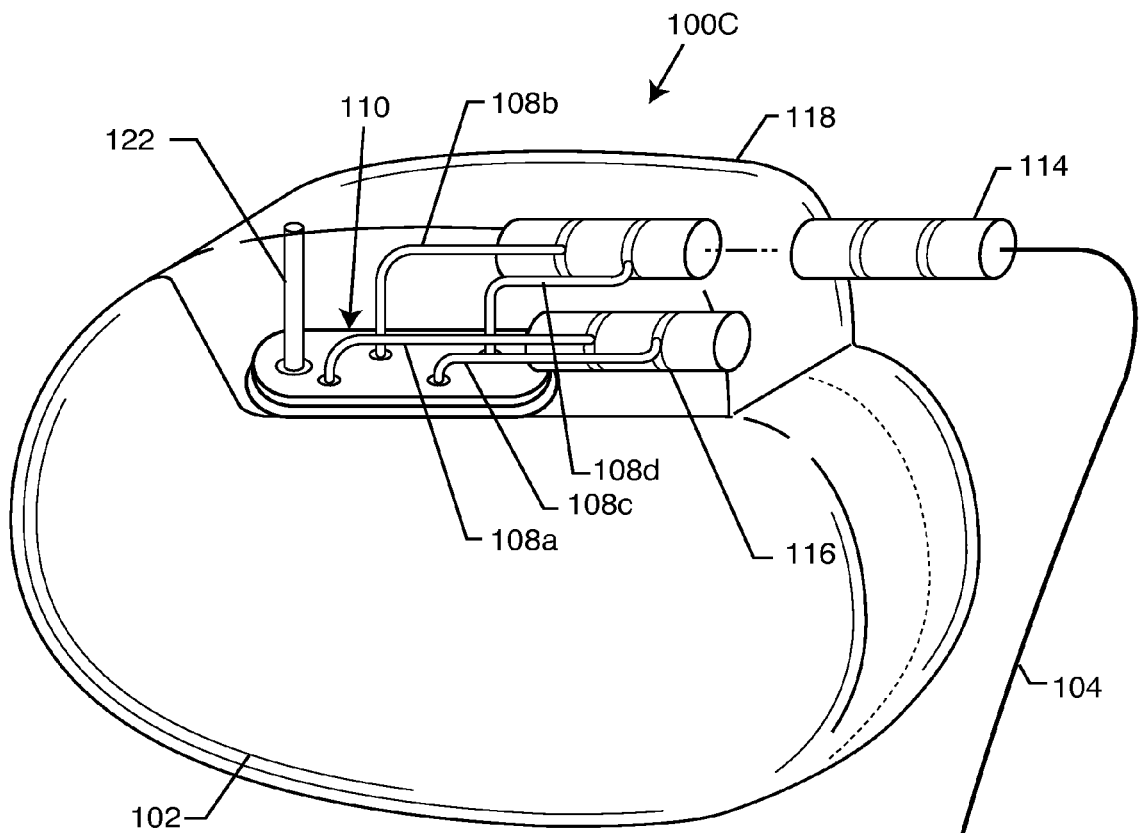
FIG. 2
PRIOR ART
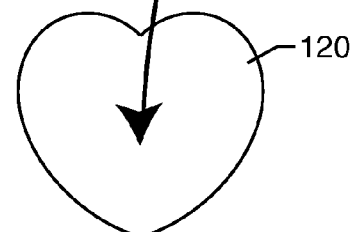

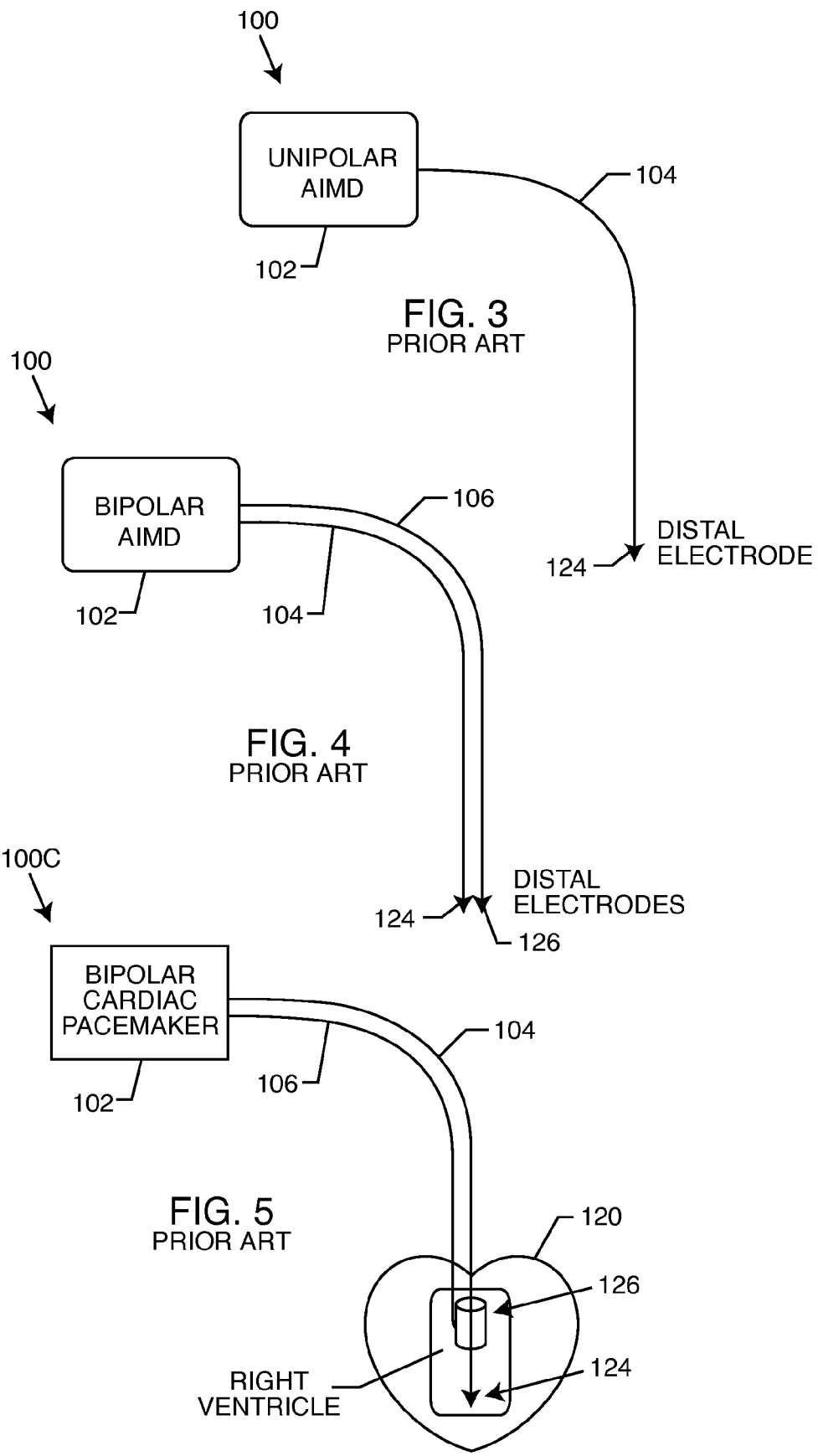

WHERE   C = CAPACITANCE IN FARADS
        L = INDUCTANCE IN HENRYS
        R = RESISTANCE (INCLUDES RESISTANCE OF INDUCTOR, HOOK-UP WIRE & CAPACITOR EQUIVALENT SERIES RESISTANCE (ESR)

RESONANT FREQUENCY = $F_r$

WHERE $F_r = \dfrac{1}{2\pi\sqrt{LC}}$

WHERE $F_r$ IS IN HERTZ $$IL_{(dB)} = 20 \log_{10} \frac{V_{REF}}{(V_2 \text{ or } V_3)}$$

Where $V_{REF}$ = Reference Circuit Voltage without Filter-Trap components $V_2$ = AIMD Input Voltage with Filter-Trap components installed $V_3$ = Voltage at AIMD electronic circuits

INSERTION LOSS

DUAL FUNCTION TUNED L-C INPUT TRAP PASSIVE EMI FILTER COMPONENT NETWORK FOR AN ACTIVE IMPLANTABLE MEDICAL DEVICE

FIELD OF INVENTION

This invention generally relates to the problem of high frequency energy induced into implanted leads during medical diagnostic procedures such as magnetic resonant imaging (MRI). Specifically, the radio frequency (RF) pulsed field of MRI can couple to an implanted lead in such a way that electromagnetic forces (EMFs) and associated RF currents are induced in the lead. The amount of energy that is induced is related to a number of complex factors, but in general, is dependent upon the local electric field that is tangent to lead and the integral of the electric field strength along the lead. In certain situations, these EMFs can cause currents to flow into distal electrodes or in the electrode interface with body tissue. It has been documented that when this current becomes excessive, that overheating of said lead or its associated electrode or overheating of the associated interface with body tissue can occur. There have been cases of damage to such body tissue which has resulted in loss of capture of cardiac pacemaking pulses, tissue damage, severe enough to result in brain damage or multiple amputations, and the like. The present invention relates generally to methods of redirecting said energy to locations other than a distal tip electrode-to-tissue interface. The redirection of this RF energy is generally done by use of frequency selective devices, such as inductors, capacitors and filtered networks. In general, this is accomplished through frequency selective low pass filters incorporating at their input (body fluid side) series resonant L-C trap filters wherein the RF energy can be redirected to the conductive housing of the active implantable medical device (AIMD) where RF or thermal energy is harmlessly dissipated. The L-C trap filters are part of the input stage of an electromagnetic interference (EMI) low pass filter. This EMI filter protects sensitive active implantable medical device (AIMD) electronics from EMI emitters such as cellular phones, microwave ovens and the like. These implantable lead systems are generally associated with AIMDs, such as cardiac pacemakers, cardioverter defibrillators, neurostimulators and the like. Implantable leads can also be associated with external devices, such as external pacemakers, externally worn neurostimulators (such as pain control spinal cord stimulators) and the like.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:
(1) Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "I. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, Patent Application Publication US 2003/0050557, Susil and Halperin et. al, published Mar. 13, 2003; and
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002.

The contents of the foregoing are all incorporated herein by reference.

However, an extensive review of the literature indicates that MRI is indeed often used with pacemaker, neurostimulator and other active implantable medical device (AIMD) patients. The safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the Scientific Sessions of the International Society for Magnetic Resonance in Medicine (ISMRM), held on 5-6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of 21 MHz to 64 MHz to 128 MHz depending upon the static magnetic field strength. The frequency of the RF pulse for hydrogen scans varies by the Lamour equation with the field strength of the main static field where: RF PULSED FREQUENCY in MHz=(MRI CONSTANT (42.56)) (STATIC FIELD STRENGTH IN TESLA). There are also phosphorous and other types of scanners wherein the MRI constant is different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 1 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and electro-magnetic interference (EMI) are induced into an implanted lead system. At very low frequency (VLF), voltages are induced at the input to the cardiac pacemaker as currents circulate throughout the patient's body and create voltage drops. Because of the vector displacement between the pacemaker housing and, for example, the tip electrode, voltage drop across the resistance of body tissues may be sensed due to Ohms Law and the circulating current of the RF signal. At higher frequencies, the implanted lead systems actually act as antennas where voltages (EMFs) are induced along their length. These antennas are not very efficient due to the damping effects of body tissue; however, this can often be offset by extremely high power fields (such as MRI pulsed fields) and/or body resonances. At very high frequencies (such as cellular telephone frequencies), EMI signals are induced only into the first area of the leadwire system (for example, at the header block of a cardiac pacemaker). This has to do with the wavelength of the signals involved and where they couple efficiently into the system.

Magnetic field coupling into an implanted lead system is based on loop areas. For example, in a cardiac pacemaker unipolar lead, there is a loop formed by the lead as it comes from the cardiac pacemaker housing to its distal tip electrode, for example, located in the right ventricle. The return path is through body fluid and tissue generally straight from the tip electrode in the right ventricle back up to the pacemaker case or housing. This forms an enclosed area which can be measured from patient X-rays in square centimeters. The average loop area is 200 to 225 square centimeters. This is an average and is subject to great statistical variation. For example, in a large adult patient with an abdominal pacemaker implant, the implanted loop area is much larger (around 400 square centimeters).

Relating now to the specific case of MRI, the magnetic gradient fields would be induced through enclosed loop areas. However, the pulsed RF fields, which are generated by the body coil, would be primarily induced into the lead system by antenna action. Subjected to RF frequencies, the lead itself can exhibit complex transmission line behavior.

At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AIMD and the length and trajectory of its associated lead(s). For example, it will make a difference how much EMF is induced into a pacemaker lead system as to whether it is a left or right pectoral implant. In addition, the routing of the lead and the lead length are also very critical as to the amount of induced current and heating that would occur. Also, distal tip design is very important as it can heat up due to MRI RF induced energy. The cause of heating in an MRI environment is two-fold: (a) RF field coupling to the lead can occur which induces significant local heating; and (b) currents induced between the distal tip and tissue during MRI RF pulse transmission sequences can cause local Ohms Law (resistive) heating in tissue next to the distal tip electrode of the implanted lead. The RF field of an MRI scanner can produce enough energy to induce RF voltages in an implanted lead and resulting currents sufficient to damage some of the adjacent myocardial tissue. Tissue ablation (destruction resulting in scars) has also been observed. The effects of this heating are not readily detectable by monitoring during the MRI. Indications that heating has occurred would include an increase in pacing threshold, venous ablation, Larynx or esophageal ablation, myocardial perforation and lead penetration, or even arrhythmias caused by scar tissue. Such long term heating effects of MRI have not been well studied yet for all types of AIMD lead geometries. There can also be localized heating problems associated with various types of electrodes in addition to tip electrodes. This includes ring electrodes or pad electrodes. Ring electrodes are commonly used with a wide variety of implanted devices including cardiac pacemakers, and neurostimulators, and the like. Pad electrodes are very common in neurostimulator applications. For example, spinal cord stimulators or deep brain stimulators can include a plurality of pad electrodes to make contact with nerve tissue. A good example of this also occurs in a cochlear implant. In a typical cochlear implant there would be sixteen pad electrodes placed up into the cochlea. Several of these pad electrodes make contact with auditory nerves. Although there are a number of studies that have shown that MRI patients with active implantable medical devices, such as cardiac pacemakers, can be at risk for potential hazardous effects, there are a number of reports in the literature that MRI can be safe for imaging of pacemaker patients when a number of precautions are taken (only when an MRI is thought to be an absolute diagnostic necessity). While these anecdotal reports are of interest, they are certainly not scientifically convincing that all MRI can be safe. For example, just variations in the pacemaker lead length and implant trajectory can significantly affect how much heat is generated. A paper entitled, HEATING AROUND INTRAVASCULAR GUIDEWIRES BY RESONATING RF WAVES by Konings, et al., Journal of Magnetic Resonance Imaging, Issue 12:79-85 (2000), does an excellent job of explaining how the RF fields from MRI scanners can couple into implanted leads. The paper includes both a theoretical approach and actual temperature measurements. In a worst-case, they measured temperature rises of up to 74 degrees C. after 30 seconds of scanning exposure. The contents of this paper are incorporated herein by reference.

The effect of an MRI system on the function of pacemakers, ICDs, neurostimulators and the like, depends on various factors, including the strength of the static magnetic field, the pulse sequence, the strength of RF field, the anatomic region being imaged, and many other factors. Further complicating this is the fact that each patient's condition and physiology is different and each lead implant has a different length and/or implant trajectory in body tissues. Most experts still conclude that MRI for the pacemaker patient should not be considered safe.

It is well known that many of the undesirable effects in an implanted lead system from MRI and other medical diagnostic procedures are related to undesirable induced EMFs in the lead system and/or RF currents in its distal tip (or ring) electrodes. This can lead to overheating of body tissue at or adjacent to the distal tip.

Distal tip electrodes can be unipolar, bipolar and the like. It is very important that excessive current not flow at the interface between the lead distal tip electrode and body tissue. In a typical cardiac pacemaker, for example, the distal tip electrode can be passive or of a screw-in helix type as will be more fully described. In any event, it is very important that excessive RF current not flow at this junction between the distal tip electrode and for example, myocardial or nerve tissue. Excessive current at the distal electrode to tissue interface can cause excessive heating to the point where tissue ablation or even perforation can occur. This can be life threatening for cardiac patients. For neurostimulator patients, such as deep brain stimulator patients, thermal injury can cause permanent disability or even be life threatening. Similar issues exist for spinal cord stimulator patients, cochlear implant patients and the like.

There is also a need to protect sensitive AIMD electronics from EMI emitters such as cellular telephones, RFID readers, microwave ovens, radars, and the like. It has been demonstrated that such emitters can disrupt sensitive AIMD circuitry, including causing complete inhibition of pacemaker output pulses. Inhibition of pacemaker output pulses can be life-threatening for a pacemaker dependent patient. An AIMD patient, who is ambulatory, can come in close proximity to a wide variety of inadvertent RF emitters. ANSI/AAMI Standard PC69 specifies EMI tests for cardiac pacemakers and implantable cardioverter defibrillators (ICDs) over the frequency range from a few hertz all the way to 3 GHz. To provide immunity over such broad frequency ranges, broadband filtering is required.

Accordingly, there is a need for novel dual function RF impeding and/or diverting circuits, which are frequency selective and are constructed of passive components for AIMDs. The purpose of these circuits is to provide EMI filtering for the sensitive circuitry of the AIMD while at the same time to re-direct MRI induced energy in an implanted lead to the AIMD housing and thereby attenuate it from reaching the distal tip electrode or its interface with body tissue. By redirecting said energy to locations at a point distant from the distal electrodes, this minimizes or eliminates hazards associated with overheating of said distal electrodes during diagnostic procedures, such as MRI. For maximum RF energy transfer out of the lead, frequency selective diverter circuits are needed which provide a very low impedance at the MRI RF pulsed frequencies between the lead circuit and the AIMD housing to decouple and transfer energy which is induced onto implanted leads from the MRI pulsed RF field to the conductive housing of the AIMD which acts as an RF energy dissipating surface. The present invention fulfills these needs and provides other related advantages.

SUMMARY OF THE INVENTION

The present invention includes dual function frequency selective impeding and diverting (decoupling) circuits which provide both EMI filtering for sensitive AIMD circuits, and also transfer energy which is induced on the implanted lead from the MRI pulsed RF field to an energy dissipating surface (EDS), namely the housing for an active implantable medical device (AIMD). In this way, RF energy can be shunted harmlessly into the AIMD housing thereby directing such energy away from a distal tip electrode.

The present invention is primarily directed to the pulsed RF field of an MRI scanner, although it also has applicability to the gradient field as well. Because of the presence of the powerful static field, non-ferromagnetic components are presently used throughout the present invention. The use of ferromagnetic components is contraindicated because they have a tendency to saturate or change properties in the presence of the main static field.

More particularly, the present invention relates to a dual function passive component network for an active implantable medical device (AIMD), comprising (1) an electromagnetically shielded AIMD housing, (2) at least one electronic sensing or therapy delivery circuit disposed within the AIMD housing, (3) a first conductive path having a series inductance, from the electronic circuit to a tissue-stimulating or biological sensing electrode at a distal end of an implantable lead, and (4) a second conductive path having a series capacitance, conductively coupled between the first conductive path and the AIMD housing. The capacitance provides at least one component of an electromagnetic interference (EMI) filter for the electronic circuit. Further, the inductance and the capacitance form a frequency selective L-C trap for diverting high frequency energy induced on the first conductive path at a selected frequency or range of frequencies to the AIMD housing through the second conductive path.

The high-frequency energy may comprise an MRI RF pulsed frequency or range of MRI RF pulsed frequencies. The center frequency of said range of MRI RF pulsed frequencies may be in megahertz and selected from the group of frequencies comprising the MRI constant times the static magnetic field strength in Teslas of an MRI scanner. For example, a 1.5 T hydrogen scanner has an MRI Lamour constant of 42.56. Accordingly, its RF pulsed frequency=(42.56)(1.5)=63.84 MHz.

The EMI filter typically comprises at least one capacitor and at least one inductor and forms a low pass filter. The low pass filter may comprise an L-C filter, a T filter, an LL filter, or an "n" element filter.

The AIMD may comprise an implantable hearing device, a neurostimulator, a brain stimulator, a cardiac pacemaker, a left ventricular assist device, an artificial heart, a drug pump, a bone growth stimulator, a urinary incontinence device, a spinal cord stimulator, an anti-tremor stimulator, an implantable cardioverter defibrillator, a congestive heart failure device, or a cardio resynchronization therapy device.

The second conductive path is capacitively coupled to the first conductive path between the inductor and the electronic circuit, and to the AIMD housing. The series inductance of the first conductive path comprises at least one inductor which may be a circuit trace or a chip inductor. The series capacitance of the second conductive path comprises at least one capacitor which may be a chip capacitor.

The capacitor may alternatively comprise a feedthrough capacitor associated with a hermetic terminal through which the first conductive path extends in non-conductive relation with the AIMD housing. In this case, the inductor is disposed exteriorly of the AIMD housing, for example, within a header block for the AIMD. When so disposed, the inductor preferably has external surfaces comprised entirely of biocompatible and non-migratable materials. Of course, the inductor and the capacitor may both be disposed within the AIMD housing.

Moreover, one or more bandstop filters may be incorporated into the passive component network of the present invention, disposing it serially along a first conductor between the primary L-C trap and the electronic circuits.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 2 is a perspective and somewhat schematic view of a prior art active implantable medical device (AIMD) including a leadwire directed to the heart of a patient;

FIG. 3 is a diagram of a unipolar active implantable medical device;

FIG. 4 is a diagram similar to FIG. 3, illustrating a bipolar AIMD system;

FIG. 5 is a diagram similar to FIGS. 3 and 4, illustrating a bipolar lead system with a distal tip and ring electrodes, typically used in a cardiac pacemaker;

DETAILED DESCRIPTION OF THE PREFERRED EMBODIMENTS

Figure 1:
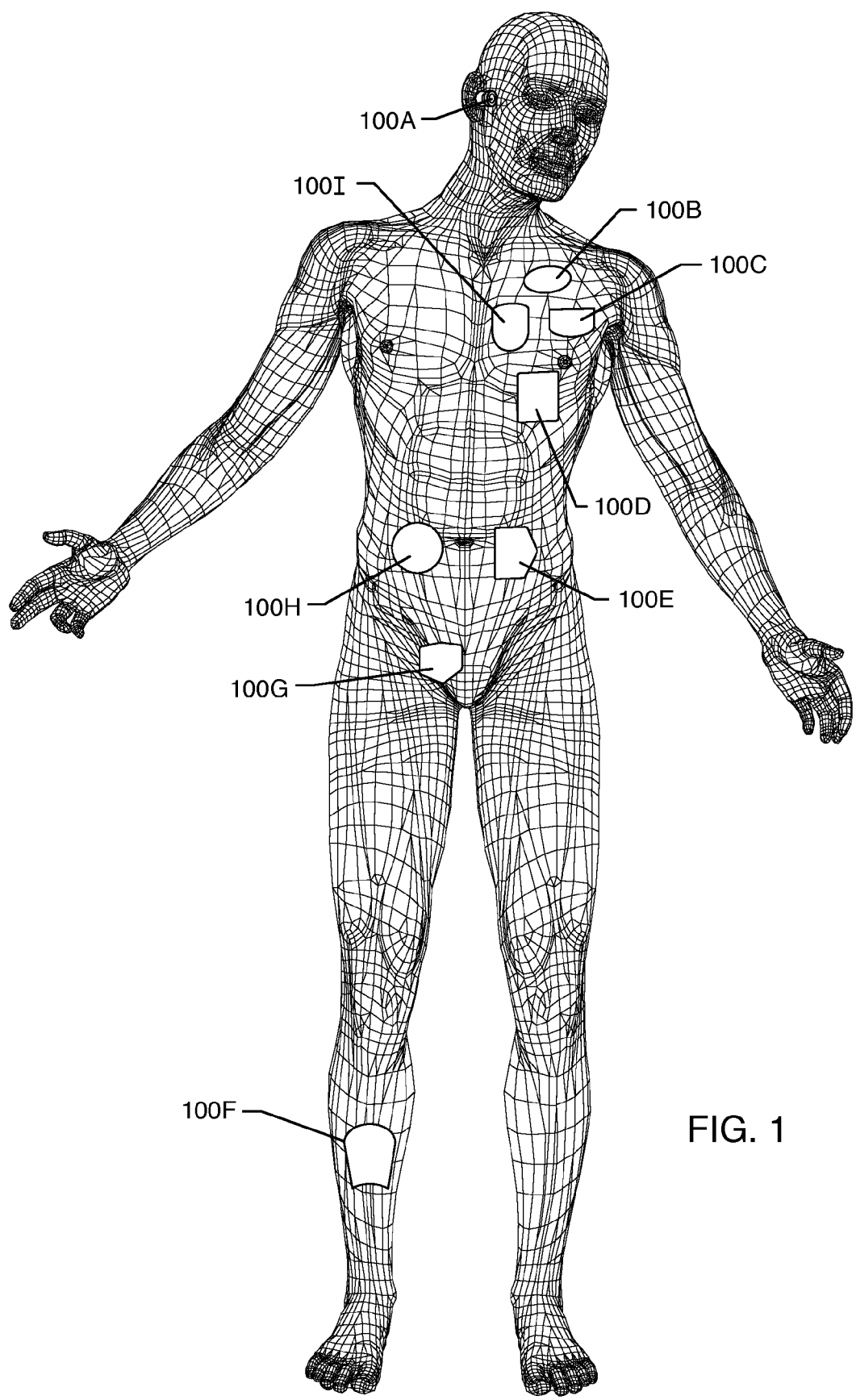
FIG. 1 is a wire-formed diagram of a generic human body showing a number of exemplary implanted medical devices.

FIG. 1 illustrates various types of active implantable medical devices referred to generally by the reference numeral 100. FIG. 1 is a wire formed diagram of a generic human body showing a number of exemplary medical devices. 100A is a family of implantable hearing devices which can include the group of cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. 100C shows a cardiac. 100D includes the family of left ventricular assist devices (LVAD's), and artificial hearts. 100E includes an entire family of drug pumps which can be used for dispensing of insulin, chemotherapy drugs, pain medications and the like. 100F includes a variety of implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillator (ICD) devices and also includes the family of congestive heart failure devices (CHF). This is also known in the art as cardio resynchronization therapy devices, otherwise known as CRT devices.

A prior art active implantable medical device (AIMD) is illustrated in FIG. 2. In general, the AIMD could, for example, be a cardiac pacemaker 100C, which is enclosed by a titanium or stainless steel conductive housing 102 as indicated. The conductive housing 102 is hermetically sealed and contains a battery and electronic circuits, however, there is a point where conductors such as the illustrative conductors 108a-108d must ingress and egress in non-conductive relationship relative to the housing 102. This is accomplished by providing a hermetic terminal assembly 110. Hermetic terminal assemblies are well known and generally consist of a ferrule 112 which is laser welded to the titanium housing 102 of the AIMD 100C. In FIG. 2, four conductors 108a-108d are shown for connection to a corresponding number of leads, such as the illustrative lead 104 shown for coupling to the conductor 108b. In this configuration, the four leads coupled respectively to the conductors 108a-108d are typical of a dual chamber bipolar cardiac pacemaker.

Connector plugs 114, commonly known as IS-1 connectors, are designed to plug into mating receptacles 116 on a header block 118 on the pacemaker housing 102. These are low voltage (pacemaker) lead connectors covered by an International Standards Organization (ISO) standard IS-1. Higher voltage devices, such as implantable cardioverter defibrillators, are covered by a standard known as the ISO DF-1. A newer standard had been published that integrates both high voltage and low voltage connectors into a new miniature quadpolar connector series known as the ISO IS-4 standard. Leads plugged into such connectors are typically routed in a pacemaker or ICD application down into the right ventricle and right atrium of the heart 120. There are also new generation devices that have been introduced to the market that couple leads to the outside of the left ventricle. These are known as biventricular devices and are very effective in cardiac resynchronization therapy (CRT) and treating congestive heart failure (CHF).

One can see, for example, the conductors 108a and 108b that could be coupled by leads and routed, for example, to distal tip and ring electrodes within the right ventricle of the heart 120. The other pair of conductors 108c and 108d could be coupled by leads and routed to distal tip and ring electrodes within the right atrium of the heart 120. There is also an RF telemetry pin antenna 122 which is not connected to the IS-1 or DS-1 connector block. This acts as a short stub antenna for picking up telemetry signals that are transmitted from the outside of the device.

It should be apparent to those skilled in the art that all of the descriptions herein are equally applicable to other types of AIMDs. These include implantable cardioverter defibrillators (ICDs), neurostimulators, including deep brain stimulators, spinal cord stimulators, cochlear implants, incontinence stimulators and the like, and drug pumps. This list is not meant to be limiting, but is only example of the applications of the novel technology currently described herein. In the following description, functionally equivalent elements shown in various embodiments will often be referred to utilizing the same reference number.

FIG. 3 is a general diagram of a unipolar active implantable medical device 100 and related system. The housing 102 of the active implantable medical device 100 is typically titanium, ceramic, stainless steel or the like. Inside of the device housing are the AIMD electronic circuits. Usually AIMDs include a primary or secondary battery, but that is not always the case. A lead 104 is routed from the AIMD 100 to a point 124 typically including or comprising an electrode embedded in or affixed to body tissue. In the case of a spinal cord stimulator 100H (FIG. 1), the distal tip 124 could be in the spinal cord. In the case of a deep brain stimulator 100B (FIG. 1), the distal electrode 124 would be placed deep into the brain, etc. In the case of a cardiac pacemaker 100C (FIG. 1), the distal electrode 124 would typically be placed in the cardiac right ventricle.

FIG. 4 is very similar to FIG. 3 except that it depicts a bipolar device 100 and related system. In this case, a first lead 104 is coupled to a first distal electrode 124, and a second distal electrode 126 and associated lead 106 provide an electric circuit return path between the two distal electrodes 124 and 126.

FIG. 5 illustrates a cardiac pacemaker 100C which has a single chamber bipolar lead system including a distal tip electrode 124 and a ring electrode 126 which floats in the blood pool. In contrast, the electrical return path in FIG. 3 is between the distal electrode 124 through body tissue to the conductive housing 102 of the implantable unipolar medical device 100.

In all of these applications, the patient could be exposed to the fields of an MRI scanner or other powerful emitter used during a medical diagnostic procedure. Currents that are directly induced in the leads 104, 106 can cause heating by $P = I^2 R$ (Ohm's law) losses in the leads or by heating caused by RF current flowing from the tip and ring electrodes 124, 126 into body tissue. If these induced RF currents become excessive, the associated heating can cause damage or even destructive ablation to body tissue.

The distal tip electrode 124 is designed to be implanted against or into or affixed to (screwed into) the actual myocardial tissue of the heart 120. The ring electrode 126 is designed to float in the blood pool. Because the blood is flowing and is thermally conductive, some people feel that the ring structure 126 is substantially cooled. However, this is only in theory. Studies have shown that upon lead removal, the entire area of the tip and the ring can become overgrown and embedded in body tissue and thereby thoroughly encapsulated. Accordingly, in some pacemaker patients, both the distal tip and ring can become thermally insulated by surrounding body tissue and can readily heat up due to the RF pulsed currents of an MRI field.

Figure 6:
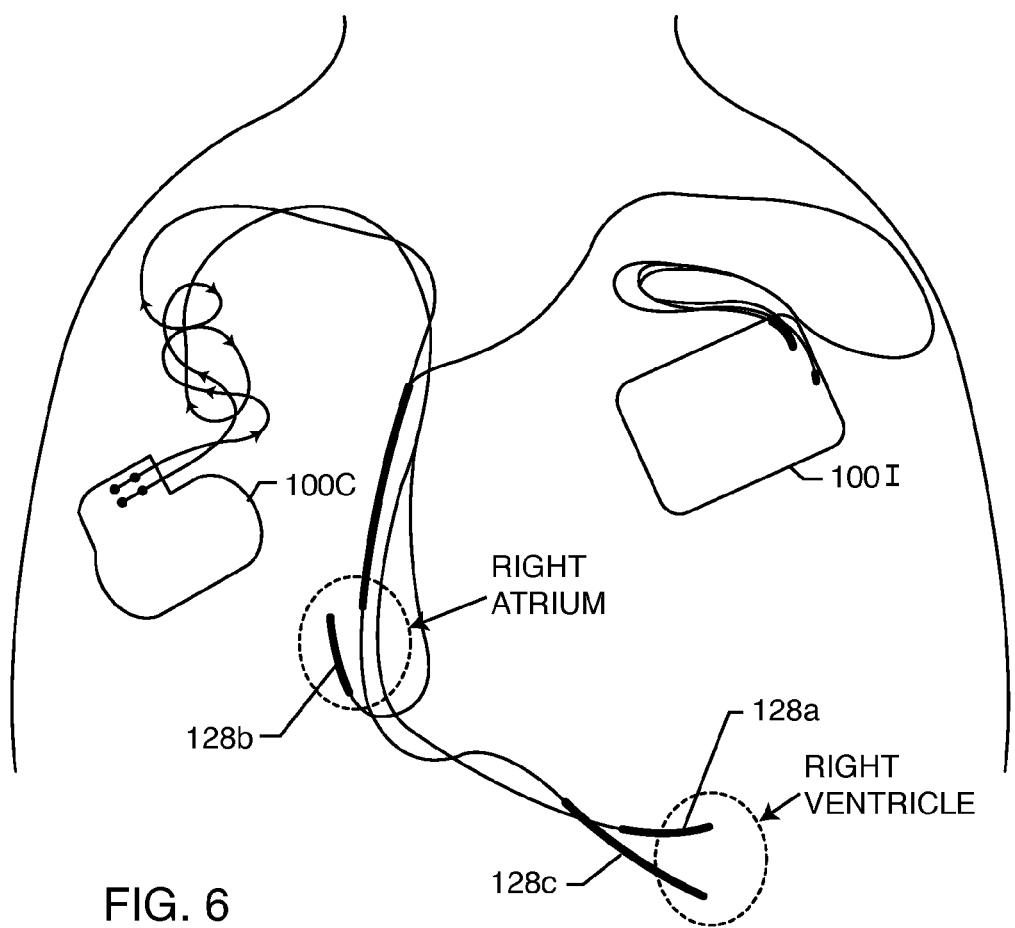
FIG. 6 is a tracing of an exemplary patient X-ray showing an implanted pacemaker and cardioverter defibrillator and corresponding lead system.

FIG. 6 is a tracing of an actual patient X-ray. This particular patient required both a cardiac pacemaker 100C and an implantable cardioverter defibrillator (ICD) 100I. The corresponding implantable leadwire system, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

In FIG. 6, one can see that from the pacemaker 100C, there is an electrode 128a and 128b in both the right atrium and in the right ventricle. Both of these are bipolar and involve a separate tip and ring electrode (not shown in FIG. 6). In the industry, this is known as a dual chamber bipolar lead system. One can also see that the implantable cardioverter defibrillator (ICD) 100I is associated with an electrode 128c implanted directly into the right ventricle. Its shocking tip and perhaps its superior vena cava (SVC) shock coil would also require the passive dual EMI filter and frequency selective diverter (L-C trap) of the present invention so that MRI exposure cannot induce excessive currents into the associated leadwires or electrodes. Modern implantable cardioverter defibrillators (ICDs) incorporate both pacing and cardioverting (shock) features. Accordingly, it is becoming quite rare for a patient to have a leadwire layout as shown in the X-ray of FIG. 6. However, the number of electrodes remains the same. There are also newer combined pacemaker/ICD systems which include biventricular pacemaking (pacing of the left ventricle). These CRT systems can have as many as 9 to even 12 leadwires.

Figure 7:
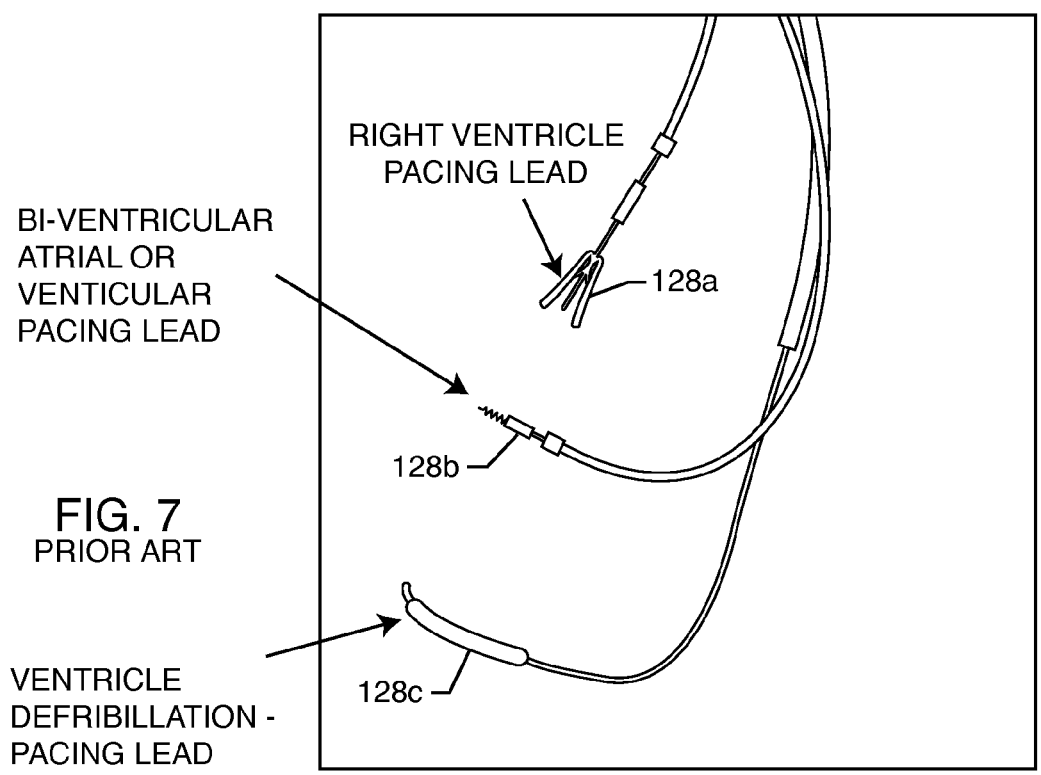
FIG. 7 is a line drawing of an exemplary patient cardiac X-ray of a bi-ventricular lead system.

FIG. 7 is a line drawing of an actual patient cardiac X-ray of one of the newer bi-ventricular leadwire systems with various types of electrode tips 128a, 128b and 128c shown. The new bi-ventricular systems are being used to treat congestive heart failure, and make it possible to implant leads outside of the left ventricle. This makes for a very efficient pacing system; however, the implantable lead system is quite complex. When a lead system, such as those described in FIGS. 2-7, is exposed to a time varying electromagnetic field, electric currents can be induced into the electrodes of such leadwire systems.

Figure 8:
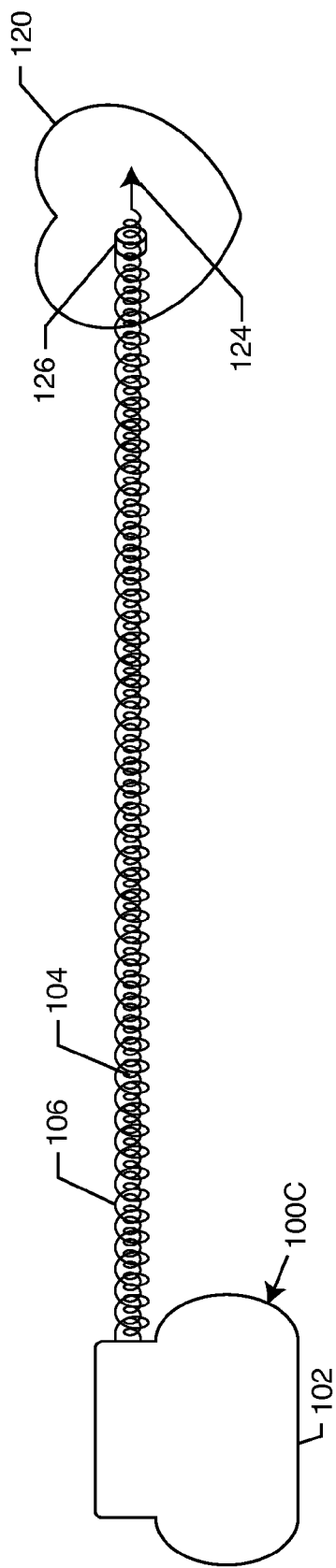
FIG. 8 illustrates a bipolar cardiac pacemaker lead showing the distal tip and the distal ring electrodes.

FIG. 8 illustrates a single chamber bipolar cardiac pacemaker 100C having a lead system and showing the distal tip 124 and the distal ring 126 electrodes. This is a spiral wound (coaxial) lead system where a ring coil lead 106 is wrapped around a tip coil lead 104, wherein these two leads 104, 106 extend between the electronic circuits inside a hermetically sealed housing 102 and the pair of electrodes 124, 126. There are other types of pacemaker lead systems in which these two leads lay parallel to one another (known as bifilar lead systems, which are not shown).

Figure 9:
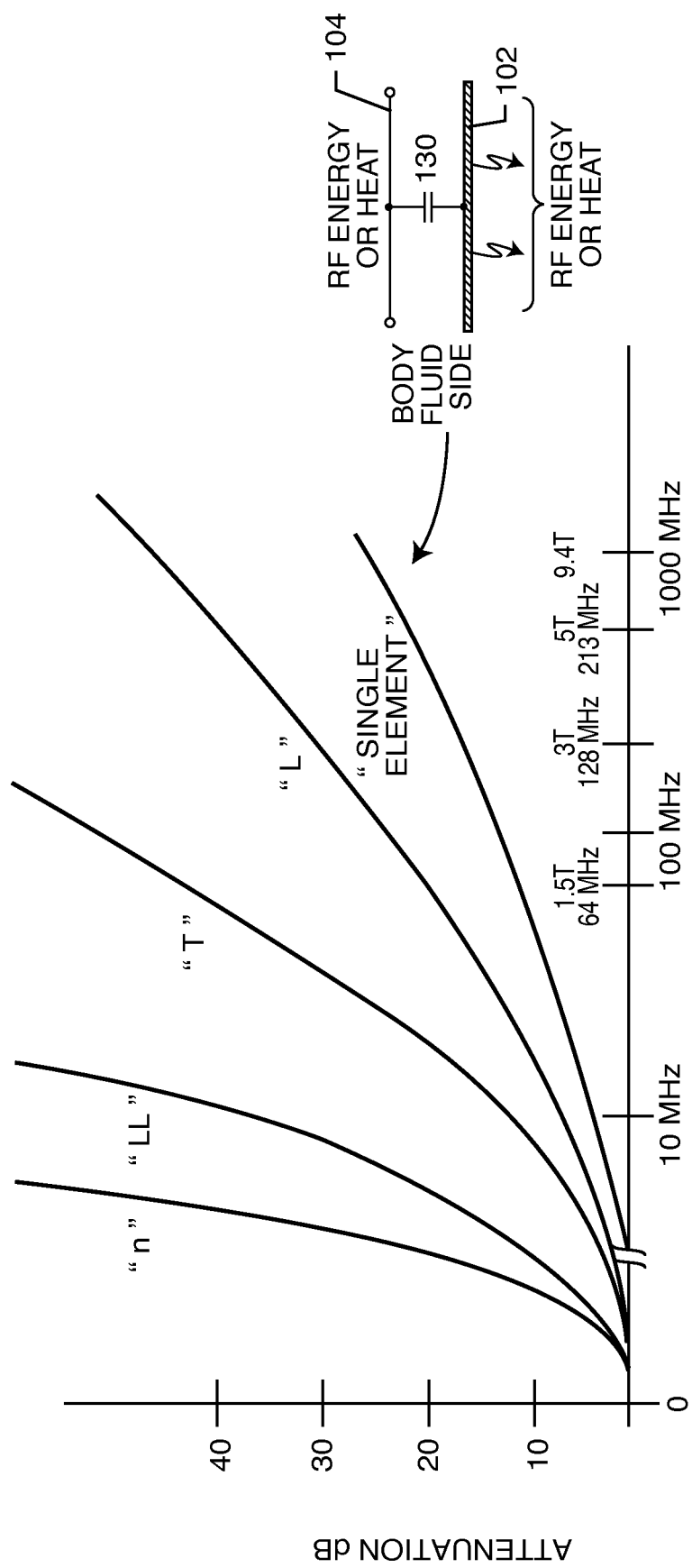
FIG. 9 is an attenuation versus frequency chart for various types of low pass filters.
Figure 10:
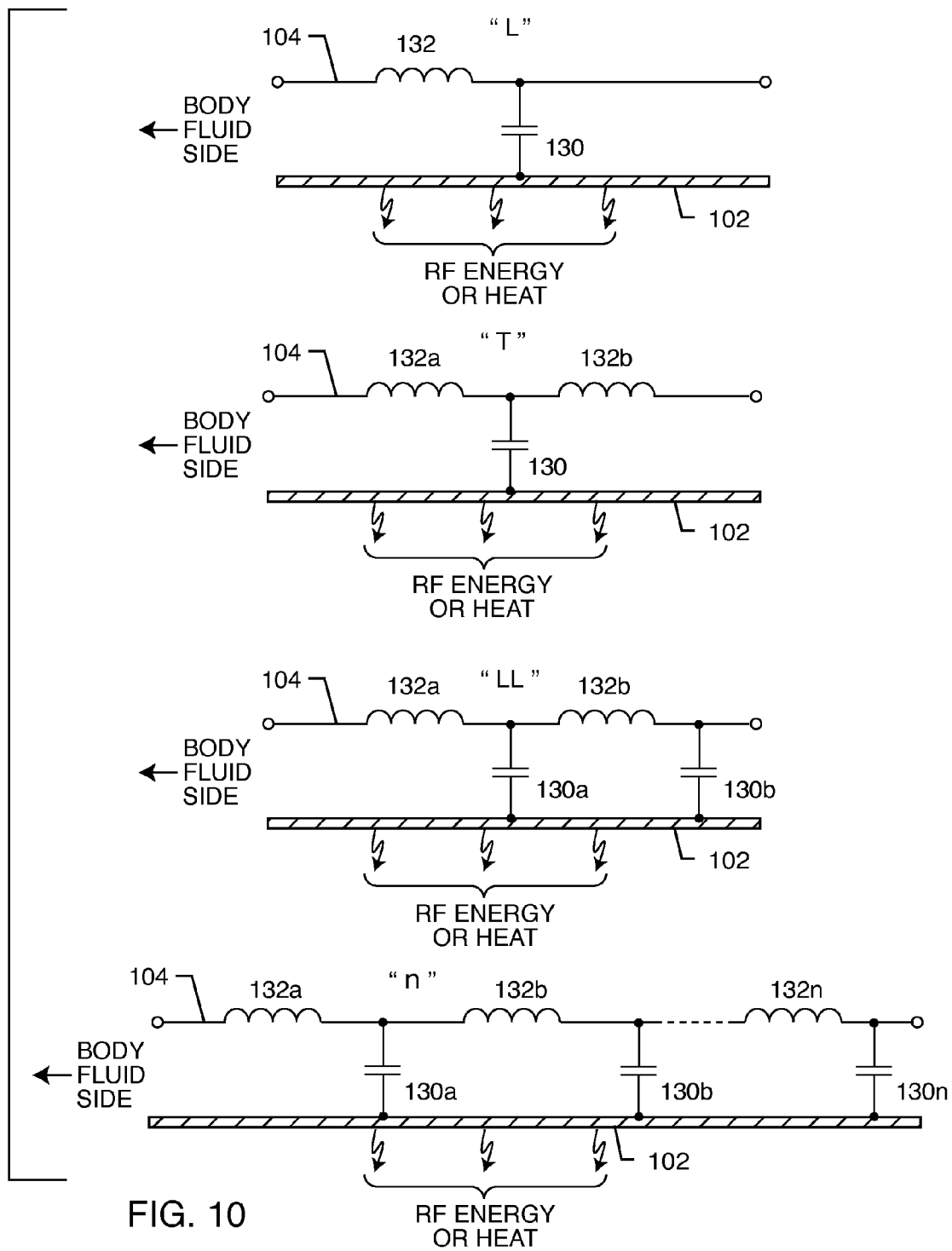
FIG. 10 shows schematic circuit diagrams for different types of low pass filters charted in FIG. 9.

Various types of AIMD low pass EMI filters are shown in FIGS. 9 and 10 which compares the filtering efficiency measured as attenuation versus frequency in dB with increasing numbers of low-pass filter elements. Also shown on the frequency axis are the common RF pulsed frequencies for 1.5 T through 9.4 T Tesla MRI scanners. Shown are a single element low pass filter consisting of a single capacitor 130, an L filter which consists of an inductor 132 and a capacitor 130, a T filter, an LL filter or an "n" element filter. In each case shown in FIG. 10, an inductor element of the present invention is directed toward the implanted lead (body fluid side).

FIG. 9 shows the general response curves of these types of filters in attenuation versus frequency. Selected schematics for these various filters, which are correlated to the curves in FIG. 9, are shown on FIG. 10. As one increases the number of EMI filter elements, the ability to attenuate or block unwanted high frequency signals from reaching sensitive AIMD electronic circuits is improved. Referring once again to FIG. 9, for example, one can see that for a particular value of a single element capacitive filter the attenuation for a 1.5 Tesla MRI system operating at 64 MHz is only about 12 dB. This means that a significant amount of the RF MRI energy would reach sensitive AIMD electronic circuits. Now compare this to the L filter where one can see that there is in excess of 22 dB of attenuation at 64 MHz. In this case, only a very small amount of RF energy from the RF pulsed frequency of the MRI, would reach AIMD electronic circuits. The inductor element 132 and the capacitor element 130 of the L filter also form a series resonant L-C trap filter between the lead 104 and the AIMD housing 102. The L-C trap filter may be tuned to be resonant at a selected MRI RF pulse center frequency. The resistive loss and Q of these components is selected so that the L-C trap filter presented a very low device input impedance over a range of selected MRI pulsed frequencies.

The present invention is embodied in a combined low-pass EMI filter and an AIMD input L-C trap filter. Filtering efficiency can be further increased by using a "T":, an "LL", or even an "n" element filter. In all these cases, the input on the body fluid side would first be an inductor followed by a first capacitor. For example, referring to the "n" element circuit (FIG. 10), inductor 132a is designed to be resonant as an L-C trap filter with capacitor 130a. The additional sections 132b and 130b could be designed to be L-C trap resonant at the same or a MRI pulsed center frequency. Accordingly, as many L-C trap filters as desired may be utilized. As can be seen in FIGS. 9 and 10, additional sections also provide additional low pass filtering in order to better protect sensitive AIMD electronics.

Figures 11, 12:
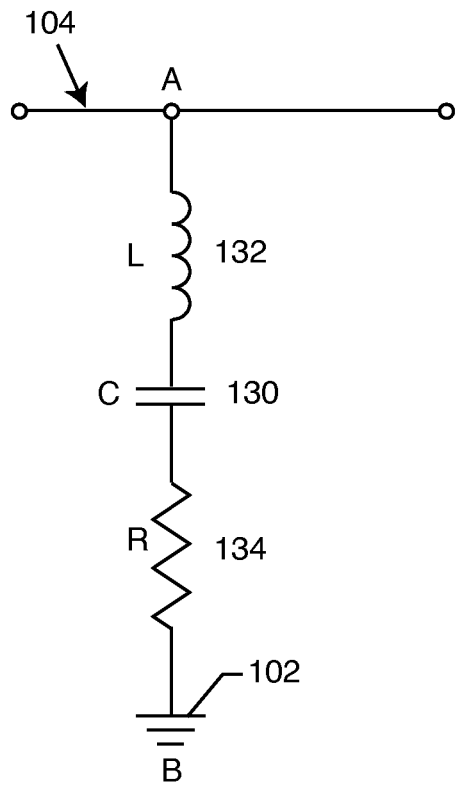
FIG. 11 is a schematic circuit diagram illustrating a prior art L-C trap filter.
FIG. 12 depicts a resonant frequency equation for the L-C trap filter of FIG. 11.

FIG. 11 illustrates a prior art schematic diagram of a series inductor (132)—capacitor (130) filter which is commonly known in the industry as an L-C trap filter. In this case, the elements of the L-C trap filter, which consists of inductor 132, capacitor 130, and parasitic resistance 134 are all wired in series and are disposed between the implanted lead circuit 104 and the AIMD housing 102. There is a particular frequency for a trap filter when the capacitive reactance becomes equal and opposite to the inductive reactance. At this single (center) frequency, the capacitive reactance and the inductive reactance cancel each other out to zero. At this resonant frequency point, all one has left is resistance 134. If one selects high quality factor (Q) components, meaning that they are very low in resistance, then the trap filter of FIG. 11 ideally tends to look like a short circuit at its resonant frequency $F_r$ between points A and B which may comprise connections respectively to an implanted lead 104. FIG. 12 gives the resonant frequency equation where $F_r$, in this case, was measured in hertz. It is important that the amount of resistance R be controlled. This is better understood by referring to FIG. 13.

Figure 13:
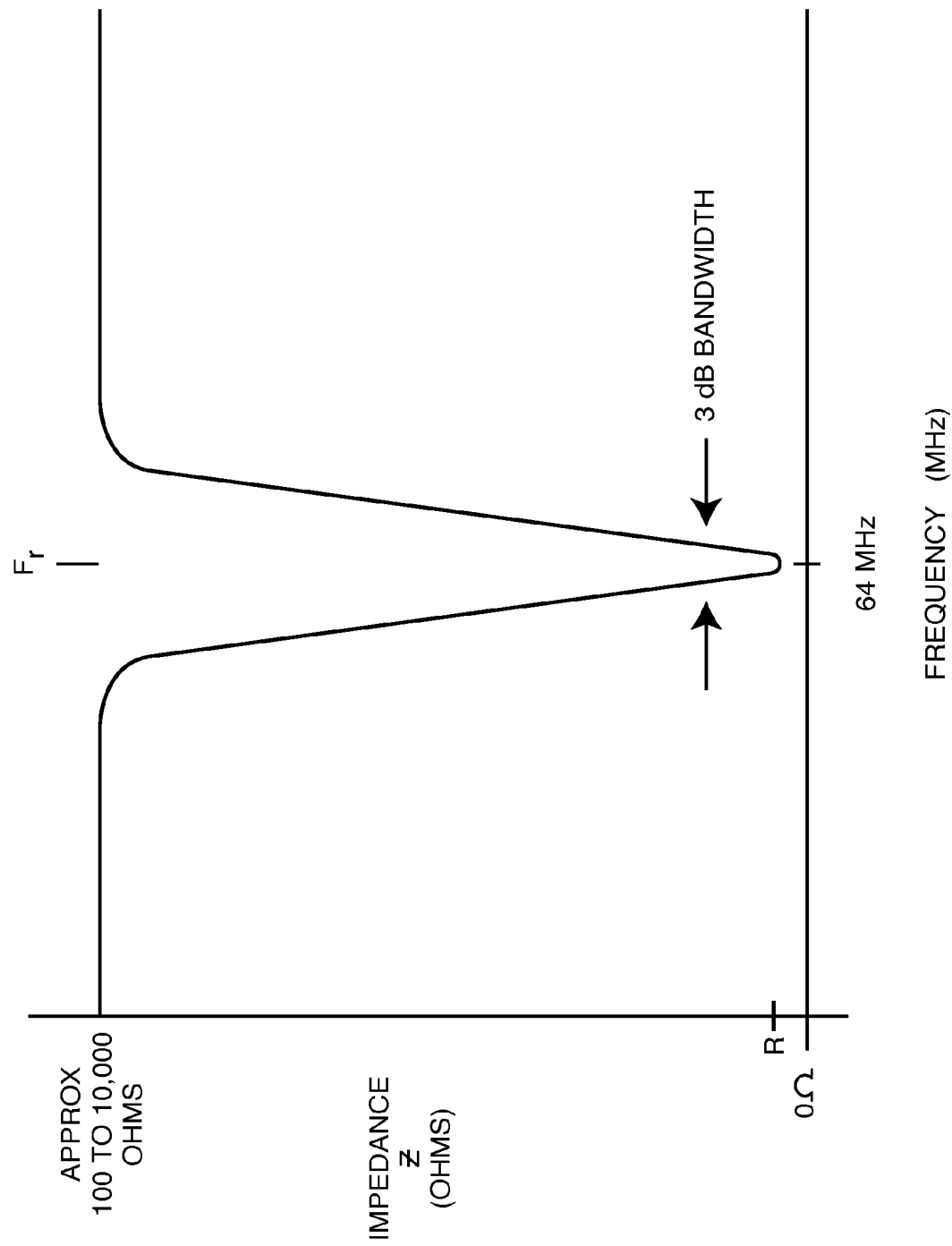
FIG. 13 is an impedance versus frequency chart for the L-C trap filter of FIG. 11.

FIG. 13 illustrates the impedance Z in ohms versus frequency of the prior art series resonant L-C trap filter of FIG. 11. As one can see, the impedance is quite high until one reaches the frequency of resonance $F_r$. At this point, the impedance of the series L-C trap goes very low (nearly zero ohms). For frequencies above or below resonance $F_r$, depending on the selection of component values and their quality factor (Q), the impedance can be as high as 100 to 1000 or even 10,000 ohms or greater. At resonance, the impedance tries to go to zero and is limited only be the amount of parasitic resistance that is generally composed of resistance from the inductor 132 and also the equivalent series resistance from the electrode plates of the capacitor 130. There is a trade off in proper selection of the components that controls what is known as the 3 dB bandwidth. If the resistance is extremely small, then the 3 dB bandwidth will be narrower. However, this makes the trap filter more difficult to manufacture. Accordingly, the 3 dB bandwidth and the resistive element are preferably selected so that it is convenient to manufacture the filter and tune it to, for example, 64 MHz while at the same time providing a very low impedance R at the resonant frequency. For an ideal L-C series resonant trap filter, wherein ideal would mean that the resistance R would be zero, then the impedance at resonance would be zero ohms. However, in this case, the 3 dB bandwidth would be so narrow that it would be nearly impossible to manufacture. Accordingly, a controlled amount of resistance R is in fact desirable.

There is a distinct disadvantage to the sole use of the prior art L-C trap filter as shown in FIG. 11 wherein the inductor L and capacitor are disposed in series between the lead 104 circuit and AIMD housing 102. That is, it is really only effective for attenuating one range of MRI RF pulsed frequencies (for example, 63.5 to 64.5 MHz for 1.5 Tesla model scanners). Accordingly, when the AIMD manufacturer would apply for its FDA conditional labeling, it could only claim compliance with 1.5 Tesla MRI scanners. There is another important disadvantage to the sole use of the L-C trap filter as shown in FIG. 11; that is, it would provide no EMI filtering to sensitive AIMD circuits other than at the one resonant frequency. Accordingly, there would be a high probability of susceptibility to AIMD electronics from other emitters, such as cellular telephones, microwave ovens and the like that operate at frequencies that would not be attenuated with an L-C trap tuned at 64 MHz. However, the L-C trap filter of FIG. 11 also offers a very important advantage in that it offers a very high degree of attenuation at this one selected frequency or frequency range and is also highly volumetrically efficient. Accordingly, there is a trade-off here. When one uses a broadband low pass filter, a broad range of frequencies is attenuated at the cost of increased size and complexity (an additional number of components). An L-C trap filter such as shown in FIG. 11 is more of a "rifle-shot" approach wherein only one selected frequency or narrow range of frequencies is attenuated. In physics, this is more efficient and tends to make the components smaller.

The present invention involves a very novel way of looking at the input circuitry of the AIMD. It will be shown that, from the point of view of AIMD electronics, the passive low pass filters described in connection with FIG. 10 provide a very high degree of EMI immunity to sensitive AIMD electronic circuits. At the same time, the inductor and capacitor elements of the low pass filters as described in FIG. 10, for example, can also be designed to be L-C trap filters from the point of view of the input (body fluid side) of the AIMD to the AIMD housing 102 (ground). This has the desired effect of providing a combined dual function passive filter that provides a high degree of EMI protection to AIMD circuitry while at the same time trapping or drawing as much induced MRI RF energy out of the lead system as possible where it is diverted through the L-C trap to the conductive AIMD housing 102. By shunting this induced RF energy to the AIMD housing, one dissipates this energy over a relatively large surface area. In addition, the AIMD electronic housing is generally implanted in an area of the body which is not particularly sensitive to thermal injury. Using a deep brain stimulator as an example, it would be far more preferable to dissipate RF energy into a pectoral muscle AIMD housing pocket than to have the same RF energy dissipated over a relatively small implanted brain electrode where thermal energy to deep brain tissues could easily result. The combined EMI filter, L-C trap filters illustrated in FIG. 10 are the preferred embodiments in that there is always a first inductor 132 directed toward the body fluid side. For example, in FIG. 10, inductor 132a is always disposed toward body fluids. As will be shown in subsequent drawings, this inductor can be located inside the AIMD housing or external to it. What is important is that this first inductor 132a forms an L-C trap along with capacitor 130a. Therefore at least one L-C trap filter is formed for maximal RF energy transfer out of the implanted lead to the housing 102 of the AIMD.

The L-C trap filter of the present invention is very novel in that it has a node disposed between its inductor and capacitor. This node is connected to AIMD circuits. This makes the combined L-C trap filter and broadband EMI low pass filter of the present invention distinctly different from the prior art as shown in FIG. 11. From the point of view of the AIMD proximal lead end (AIMD input), the inductor and the capacitor of the present invention are in series when referenced to the AIMD housing 102. However, from the point of view of sensitive AIMD circuitry, the inductor and capacitor of the present invention form a two or multi-element low pass EMI filter. In the preferred embodiment, the inductor and capacitor elements would be constructed of passive components.

The word passive is very important in this context. Active electronic circuits, which are defined as those that require power, do not operate very well under very high intensity electromagnetic field conditions. Active electronic filters, which generally are made from microelectronic chips, have very low dynamic range. Extremely high RF signal levels induced in leads from an MRI scanner would tend to saturate such active filters and make them become nonlinear and ineffective. Passive component elements are capable of handling very high power levels without changing their characteristics or saturating. Moreover, the inductor elements are preferably made from materials that are not ferromagnetic. The reason for this is that MRI machines have a very powerful main static magnetic field ($B_0$). This powerful static magnetic field tends to saturate ferrite elements and would thereby change dramatically the value of the inductance component. Accordingly, virtually all inductor elements of the present invention are preferably fabricated without the use of ferrites, nickel, iron, cobalt or other similar ferromagnetic materials that are commonly used in general electronic circuit applications.

Figure 14:
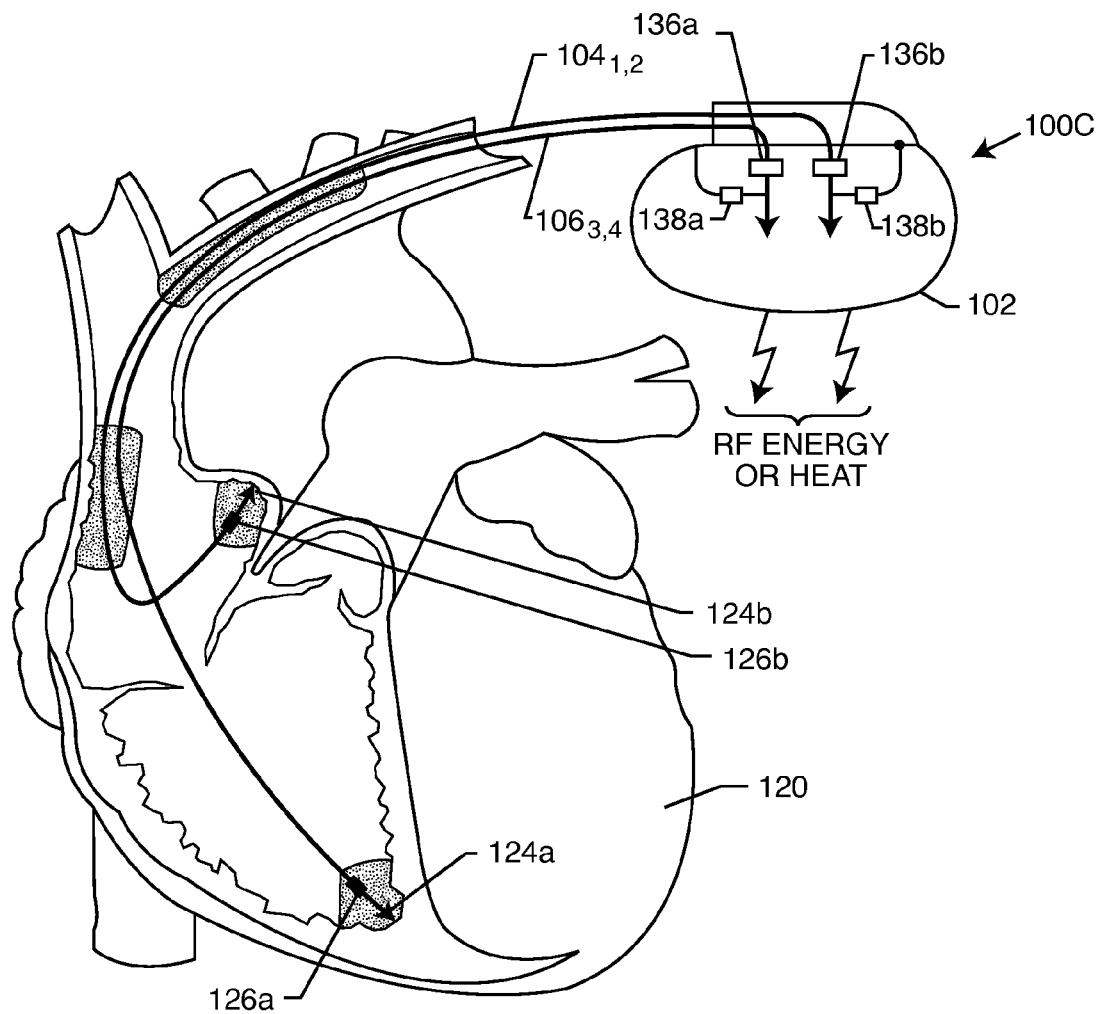
FIG. 14 is a schematic illustration of a human heart and an associated cardiac pacemaker embodying the present invention.

FIG. 14 shows a cross-sectional view of a human heart 120. Shown is a active implantable medical device such as a cardiac pacemaker 100C with bipolar leads 104 and 106 implanted into chambers of the human heart. Bipolar lead 104 is implanted into the right atrium terminating in a distal Tip electrode 124b and a distal Ring electrode 126b. Bipolar lead 106 is also implanted transvenously into the right ventricle terminating in a distal Tip electrode 124a and distal Ring electrode 126a. The shaded areas show areas where the leads tend to be entrapped by tissue encapsulation over time. The present invention is also applicable to epicardial leads which may be placed on the outside of the human heart. The cardiac pacemaker 100C is contained within a hermetically sealed conductive housing 102. The conductive housing in the prior art is typically of titanium, stainless steel or the like. In the present application, the conductive housing 102 also acts as an EMI shield and energy dissipating surface. Shown disposed inside of the conductive housing 102 of the AIMD 100C are frequency selective diverter elements 138 and impeder elements 136 of the present invention. In this case, there would be a total of four impeders and four diverters as one is generally required in each leadwire of the implanted leads. Each bipolar lead has two leadwires associated with it for the Tip and Ring circuits.

In general, the impeder is an inductor and the diverter is a capacitor so that both an L-C trap filter and a low pass filter are formed in accordance with the present invention.

Figure 15:
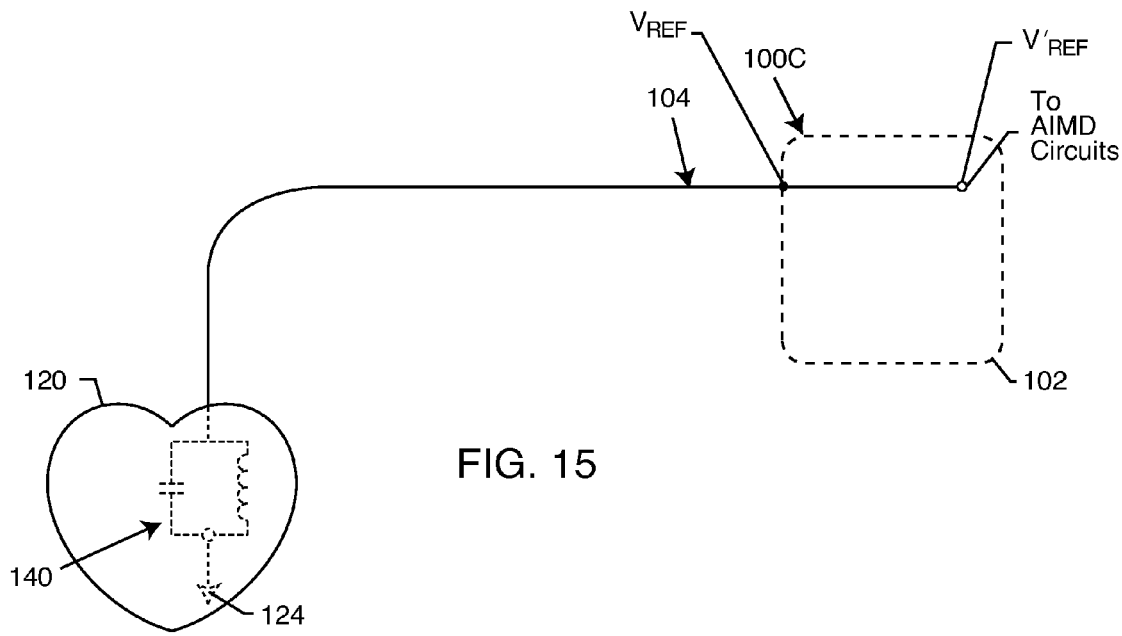
FIG. 15 is an electrical schematic illustration of a lead from AIMD circuits to the heart, without any impeding or diverting network components.

FIG. 15 is a schematic reference circuit without any filtering or trap components present. In the presence of an MRI environment, MRI RF pulsed energy would be coupled onto the implanted lead 104. This energy would appear as a voltage $V_{REF}$ at the input to the hermetic terminal assembly of the active implantable medical device (AIMD) housing 102. Since there are no components in between, $V_{REF}'$ which is at the input to AIMD electronic circuits, would be approximately equal to $V_{REF}$ (Kirchoff's voltage law). It will be appreciated that in the illustrated embodiment of FIG. 15, the electromagnetically shielded housing 102 of the AIMD 100C does not dissipate RF energy or heat. This is because there is no coupling energy diverting mechanism between $V_{REF}$ or $V_{REF}'$ and the AIMD housing 102.

Figure 16:
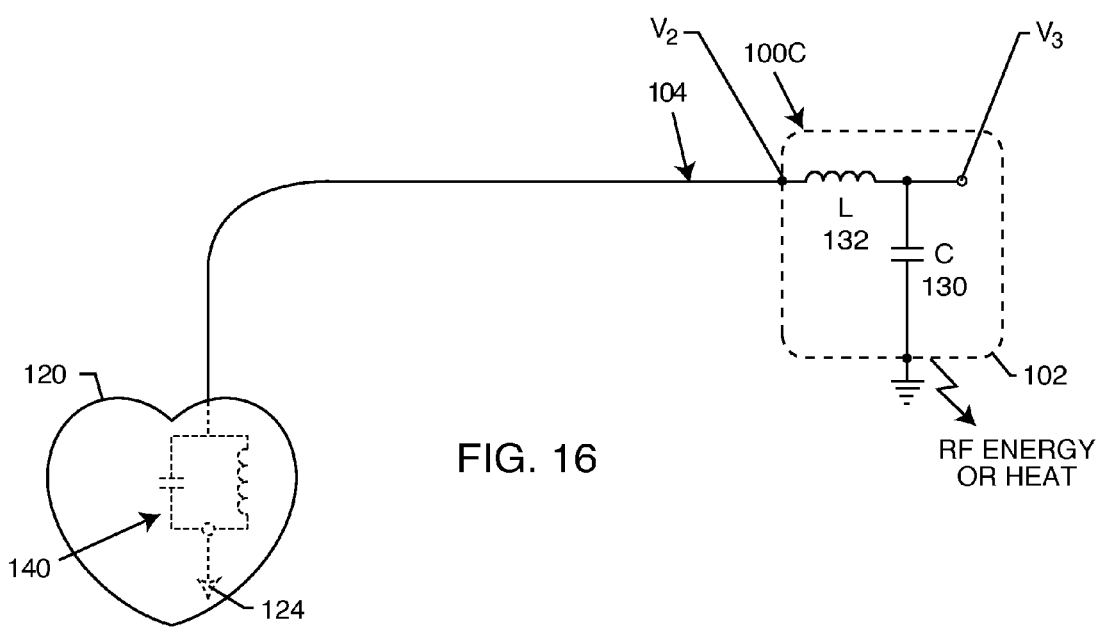
FIG. 16 is similar to FIG. 15, illustrating an inductance and a capacitance disposed to form an L-C trap in accordance with the present invention.

FIG. 16 is a schematic diagram of the present invention, wherein an inductance L (132) and a capacitance C (130) are disposed so as to, in contrast to FIG. 11, form a dual EMI filter and L-C trap. The inductance L can be formed from a discrete inductor chip, a toroidal inductor, a solenoid inductor, or any other type of discrete inductor component. The inductor L could also be formed from the inductances of the circuit itself. For example, L could be formed through the inductance of a flex cable or through circuit trace elements, such as a Wheeler spiral or the like. In addition, the inductance L need not be on the inside of the shield AIMD housing 102 as will be subsequently shown. In a preferred embodiment, the capacitance element C would be either a ceramic monolithic ceramic chip capacitor, a discoidal ceramic capacitor, or a parasitic capacitance as described in US 2009/0243756, the contents of which are incorporated by reference.

In FIG. 16 there are two voltages $V_2$ and $V_3$. Both of these voltages are different than the $V_{REF}$ voltages of FIG. 15. This is because the L and C components affect both these voltages.

Also, in FIG. 16 the conductive housing 102 of the AIMD 100C is now designated as an RF energy or heat dissipating surface. The RF energy or heat dissipation designation is directed towards the powerful pulsed RF energy of a typical MRI scanner. This RF energy is picked up by the implanted lead 104. As will be seen, the L and C components are designed to be series resonant (an L-C trap filter) with a center frequency defined by the MRI Lamour equation. The Lamour equation tells us that the frequency of the pulsed RF field is equal to the MRI constant times the static magnetic field strength of the clinical scanner in Teslas. This frequency is approximately 64 MHz for a typical prior art 1.5-Tesla hydrogen scanner. However, not all labeled 1.5-Tesla scanners are the same. There is considerable variation in the static magnetic field strength from different manufacturers. In fact, there are several hundreds of kilohertz or even a half megahertz of difference between various scanner manufacturers. Accordingly, the L-C trap in the input, as shown in FIG. 16, is designed to be resonant at a center frequency, representing the center of a range of RF pulsed frequencies. As shown in FIG. 11, a resistance element 134 is added in order to increase the 3 dB bandwidth of the L-C trap filter. FIG. 13 is a curve which illustrates the 3 dB bandwidth. This resistance element can be a discrete resistor or it can be formed from the lead wires or circuit traces as a parasitic element that forms the inductance L itself. For simplicity, this resistance element is not shown in FIG. 16 and the subsequent drawings. However, it will be understood that the L-C input trap filter of FIG. 16 is designed to attenuate over a range of MRI RF pulsed frequencies on the order of tens of kilohertz, hundreds of kilohertz, or even megahertz.

The conductive housing 102 is typically of titanium or stainless steel which has been laser welded to form a hermetically enclosed structure which is also an electromagnetic interference shield. Accordingly, the electronic circuits that are disposed inside of the AIMD housing are protected both from body fluid and from direct radiation of electromagnetic interference. In accordance with the present invention, the conductive housing 102 acts as an energy dissipating surface (EDS). Using the AIMD housing 102 itself as an energy dissipating surface is particularly effective. The first reason is that compared to the distal electrode, the AIMD housing tends to be relatively very large in surface area. Therefore it can distribute RF induced energy over this relatively large surface area with very little temperature rise. The other reason using the AIMD housing 102 as an EDS surface is important is that it is generally located far from sensitive body tissues. For example, in the case of cardiac pacemakers, the AIMD 100C would typically be located in a pectoral muscle pocket or in fatty tissue just below the pectoral skin's surface. This is far removed from the relatively more sensitive cardiac tissues. The same is particularly true of a spinal cord stimulator or a deep brain stimulator. The AIMD housing or pulse generator housing itself is located far from the spinal cord nerve root tissues or from deep brain tissues. Having a few degrees temperature rise in a muscle or fat is far preferable to having a temperature rise inside the brain tissue.

Figures 17, 18:
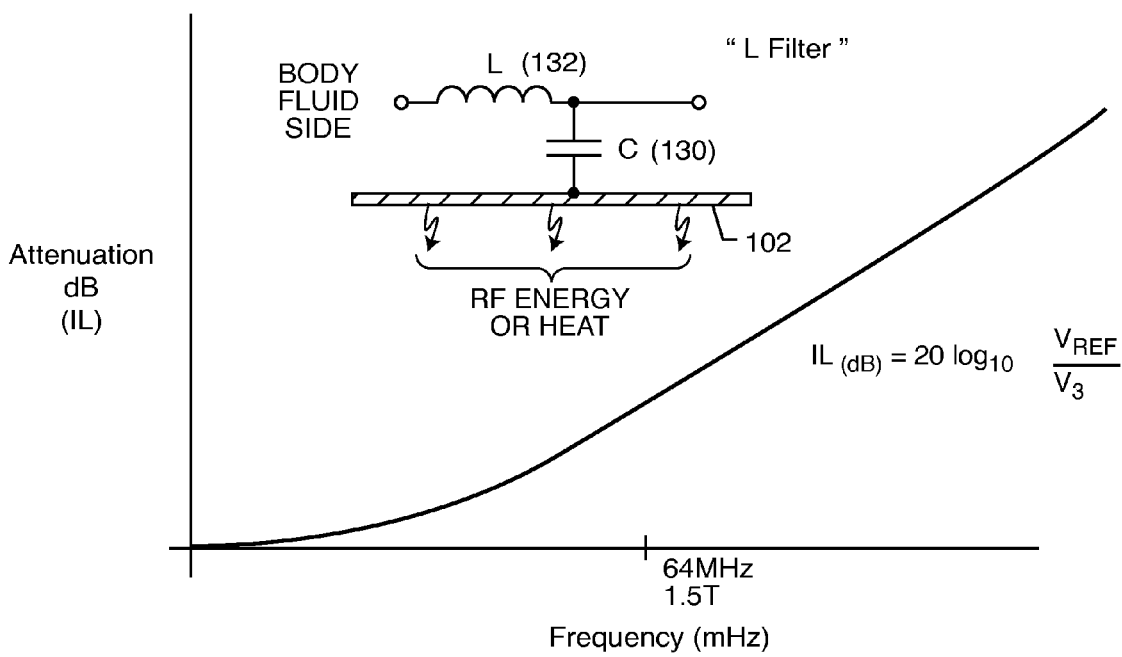
FIG. 17 is a chart illustrating the equation for insertion loss.
FIG. 18 is an attenuation versus frequency curve for the L-section EMI filter shown in FIG. 16.

Referring once again to FIG. 16, the dashed line 102 represents the AIMD hermetically sealed and conductive housing. Located within it is an inductor L (132) and capacitor C (130) of the present invention. The L and C elements for an L-C trap and a two-element EMI low pass filter. Lead 104 is directed from the AIMD into body tissues. In this case, it is directed to cardiac tissues. Shown is an optional bandstop filter 140 which in a particularly preferred embodiment works ideally with the present invention. The operation of the bandstop filter is more thoroughly described in U.S. Pat. No. 7,363,090, the contents of which are incorporated herein. The bandstop filter 140 presents a high impedance between the implanted lead and body tissue. Accordingly, RF energy that may be induced on the implanted leads from MRI imaging procedures is impeded from flowing into the cardiac tissue. The energy dissipating surface 102 of the present invention works in concert with this. RF energy is still present in the lead, but because of the bandstop filter 140, it is impeded from flowing into myocardial tissue. Therefore, it is redirected or reflected to the AIMD housing 102 by means of the novel L-C trap/EMI filter of the present invention, which is preferably designed to be resonant at a selected MRI RF pulse frequency or frequency range. Multiple L-C trap filters may be used to divert multiple MRI frequencies or ranges of frequency. The AIMD housing 102 acts as an RF energy dissipation surface FIG. 17 is the equation for insertion loss (sometimes referred to as attenuation). As one can see, this is a logarithmic function that depends on the difference between the voltage with no filter components ($V_{REF}$ in FIG. 15) and the voltages in the circuit with the filter components present ($V_2$ and $V_3$ in FIG. 16). In FIG. 15, there is only one $V_{REF}$ voltage. In FIG. 16, there are two different RF voltages, $V_2$ and $V_3$. In accordance with the present invention, the L and C components illustrated in FIG. 16 serve two very important functions. For voltage $V_2$, the L-C components form a trap filter wherein energy is diverted from the implanted lead to the conductive housing 102 of the AIMD 100C where it is dissipated as RF energy or heat. Simultaneously, from the viewpoint of the input or output of AIMD electronic circuits at $V_3$, then the L and C components act as a two-element EMI low pass filter, otherwise known in the art as an L-section EMI filter. The L and C elements are therefore, dual purpose.

FIG. 18 gives the attenuation curve for the L-section EMI filter shown in FIG. 16. As one can see, the attenuation in dB for RF voltage $V_3$ increases with frequency. This provides a high degree of EMI protection to AIMD circuits from high frequency emitters, including cell phones, microwave ovens and of course, MRI RF pulsed frequencies.

Figure 19:
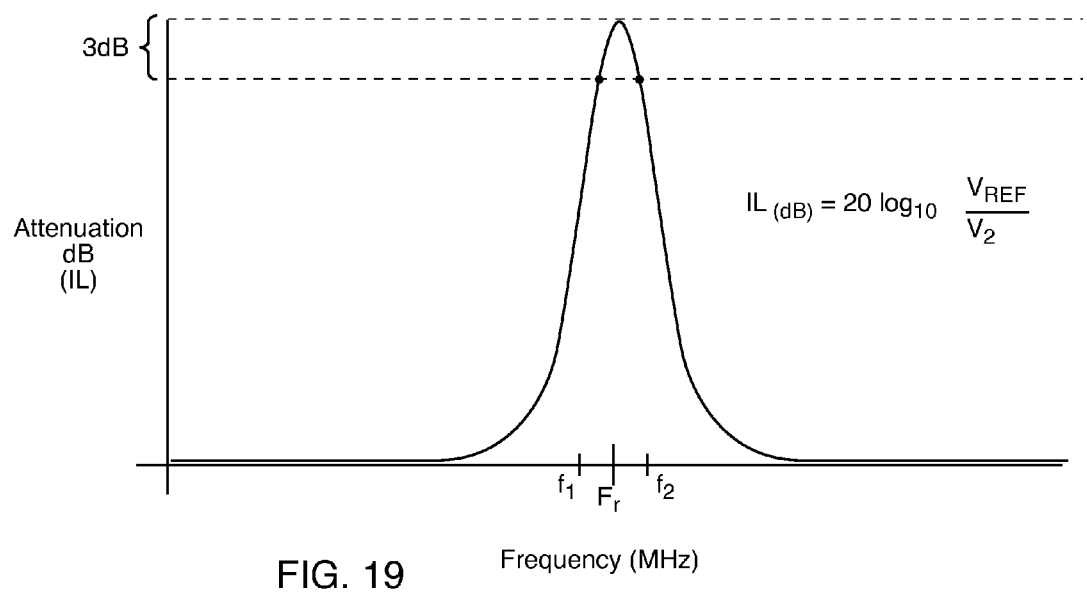
FIG. 19 shows the attenuation versus frequency with reference to input voltage V2 from FIG. 16.

FIG. 19 shows the attenuation versus frequency with reference to the input voltage $V_2$. As one can see, $V_2$ would remain relatively constant until one reaches the resonant frequency range of the L-C trap filter to the AIMD housing. At resonance, this L-C trap filter tends to look like a very low impedance (short circuit) which pulls RF induced MRI energy from the implanted lead 104 and causes it to be directed to the conductive housing 102 of the AIMD where the RF energy is dissipated. Referring once again to FIG. 19, one can see that there are 3 dB down points referenced to the center frequency $F_r$. The 3 dB bandwidth is the difference between $f_2$ and $f_1$. This results in a controlled amount of attenuation over a range of MRI frequencies. This 3 dB bandwidth range of frequencies would typically be in the order of kilohertz or megahertz. Since the AIMD housing 102 is relatively large, a relatively small temperature rise will occur. Accordingly, the novel L and C circuit of FIG. 16 acts in two very important ways. First, at MRI pulsed frequencies it lowers the input impedance of the AIMD down to a very low level in order to draw maximal RF induced energy from the lead and dissipate it as RF energy or heat from the AIMD housing 102 to tissue interface. For a cardiac pacemaker, the AIMD housing 102 would typically be located in a pectoral muscle pocket where dissipating some energy is greatly preferred over dissipating a similar amount of RF energy over relatively small surface area of an implanted electrode in myocardial tissue or even deep brain tissue. Second, the L and C two-element low pass filter provides EMI filter protection for sensitive AIMD circuits.

Figure 20:
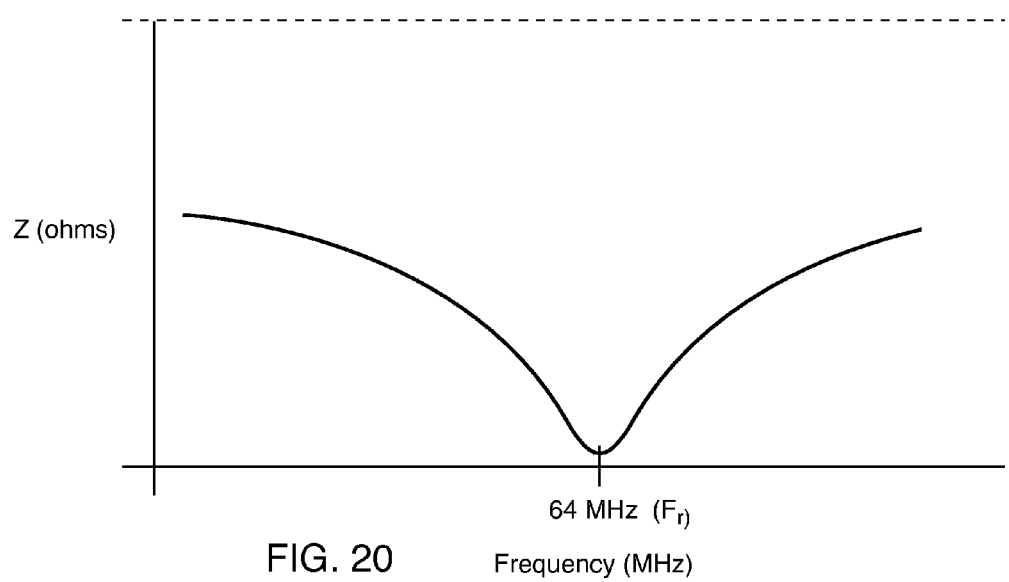
FIG. 20 illustrates the input impedance curve versus frequency of the AIMD of FIG. 16.
Figure 22:
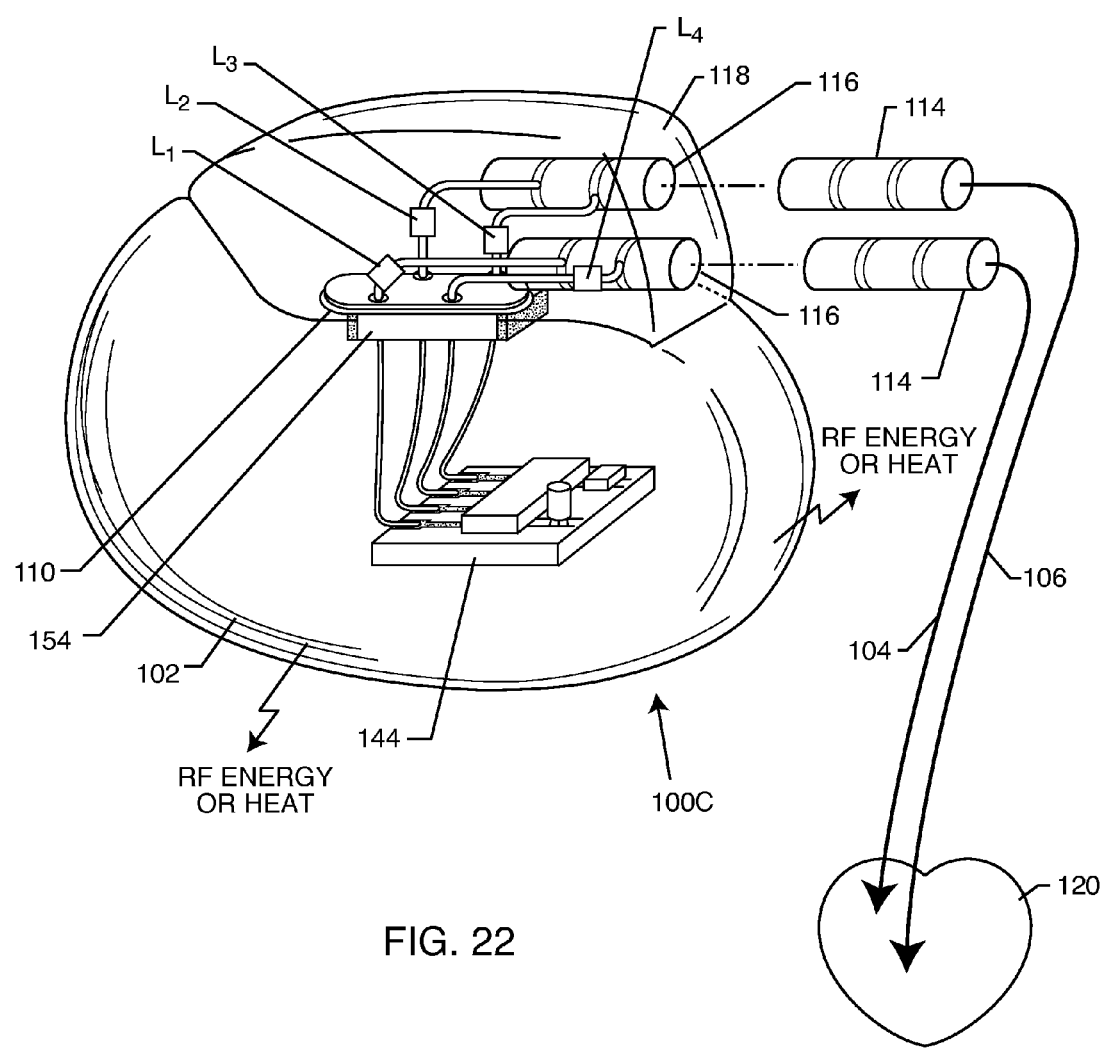
FIG. 22 is similar to FIG. 21, except that a feedthrough capacitor is used and the inductor elements are shown disposed on the body fluid side of the AIMD housing.

FIG. 20 illustrates the input impedance curve ($Z_{ohms}$) vs. frequency of the AIMD of FIG. 16. The AIMD input impedance is defined as the impedance looking from the body fluid side at the proximal lead end into the AIMD. In general, this would be the input impedance looking into the device at voltage point $V_2$, as illustrated in FIG. 16. Or, the impedance looking into the device from ports 116, as shown in FIG. 22. One can see that the input impedance is fairly high at low frequency, then as one approaches the center resonant frequency of the L-C trap the input impedance tends to go very low (acts as a short circuit), and then after resonance it climbs back up again. This is a very desired response in that at the RF pulsed frequency for MRI (shown as 64 MHz in this case), the device input impedance will look very low which means that a relatively large amount of RF induced energy will be drawn from the implanted lead 104 and redirected to the AIMD device housing 102 where it will be dissipated as harmless RF energy or heat.

Figure 21:
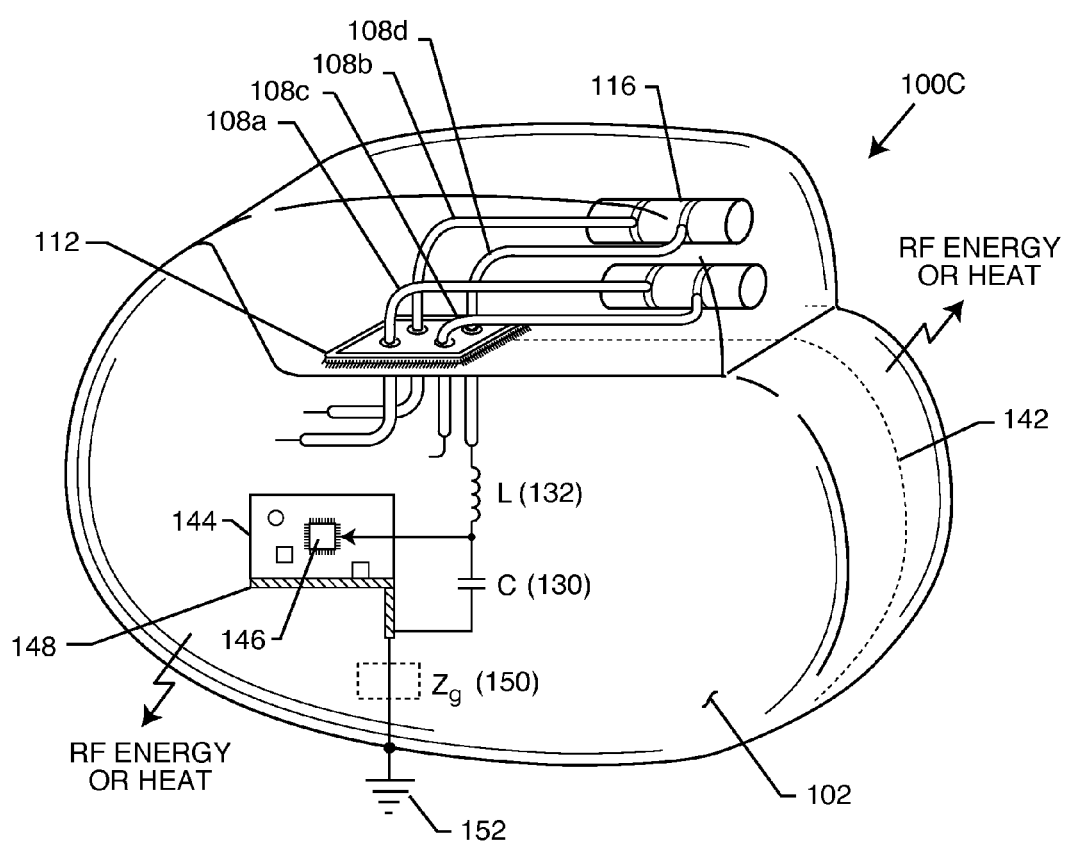
FIG. 21 is a perspective and partially diagrammatical view of a pacemaker or implantable defibrillator including the circuit of FIG. 16.

FIG. 21 is a diagrammatic view of a quadpolar pacemaker 100C, otherwise be known as a dual chamber bipolar device. There is only one L and C component shown connected in the conductor 108d circuit. There would be three more L and C combinations associated with conductors 108a-108c. These are not shown for clarity in this illustration. Also shown are the inductance L (132) and the capacitance C (130) elements along with a circuit board 144 which contains pacemaker active electronic circuits 146. Typically, the circuit board 144 will have a ground 148 as shown. In some AIMDs, the circuit trace may be directly connected to the housing 102 of the AIMD where it is shown with a ground symbol 152. In other cases, there may be a significant impedance $Z_g$ (150) in the ground circuit trace. In fact, this function is often programmable wherein in some cases, the AIMD housing 102 can act as one of the electrodes. The L and C components illustrated in FIG. 21, act exactly as previously described for FIG. 16. One can see that $Z_g$ is a desirably low impedance and the L and C are resonant and form an L-C trap, that MRI RF energy would be coupled from the implanted lead 104, 106 (not shown) via connector 116 and conductor 108d directly to the tissue ground point 152. In accordance with the present invention, this will redirect MRI RF induced energy from the implanted lead through the L-C trap filter directly to the AIMD housing 102 to surrounding pocket tissues and thereby redirect it away from a distal electrode in contact with more sensitive body tissue. By doing this, it also redirects (filters) said energy away from the sensitive active electronics 146 of circuit board 144. At other frequencies, such as microwave oven frequencies or cellular telephone frequencies, the L and C elements act as a two-element low pass filter, as described in FIG. 16. Any type of inductor input low pass filter, such as those shown in FIG. 10, could be utilized for this purpose. However, to redirect maximum energy from an implanted lead, it is important that the first inductor be towards the body fluid side, and the first capacitive element are designed to be resonant with the first inductor as an L-C trap at MRI RF pulsed frequencies as described in connection with FIGS. 16 and 21.

FIG. 22 is very similar to FIG. 21 except the inductor elements $L_1$, $L_2$, $L_3$, and $L_4$ are shown disposed outside (on the body fluid side) of the hermetically sealed AIMD housing 102. In this case, they are disposed within the header block 118 of the AIMD 100C. Such header blocks are well known in the prior art and generally conform to ISO Standards, IS-1, DF-1, IS-4, or DF-4. When the inductor is disposed outside of the hermetically sealed housing 102 of the AIMD, it must be constructed of non-toxic and biocompatible materials and connections. Biocompatible inductors and connections are described in US 2010/0023000, the contents of which are incorporated herein. A feedthrough capacitor 154 is shown, which is well known in the art as single element capacitive EMI filter. Feedthrough capacitors are described in U.S. Pat. Nos. 5,333,095, 5,905,627, and 6,765,779. By disposing the inductance on the outside of the hermetic terminal 110 of the AIMD housing, one can then use a feedthrough capacitor 154 to form the novel dual purpose L and C circuit of the present invention. As described, this circuit acts as an L-C trap as far as the AIMD input impedance is concerned and also acts as a broadband low pass filter as far as protection of AIMD electronics is concerned.

Figure 23:
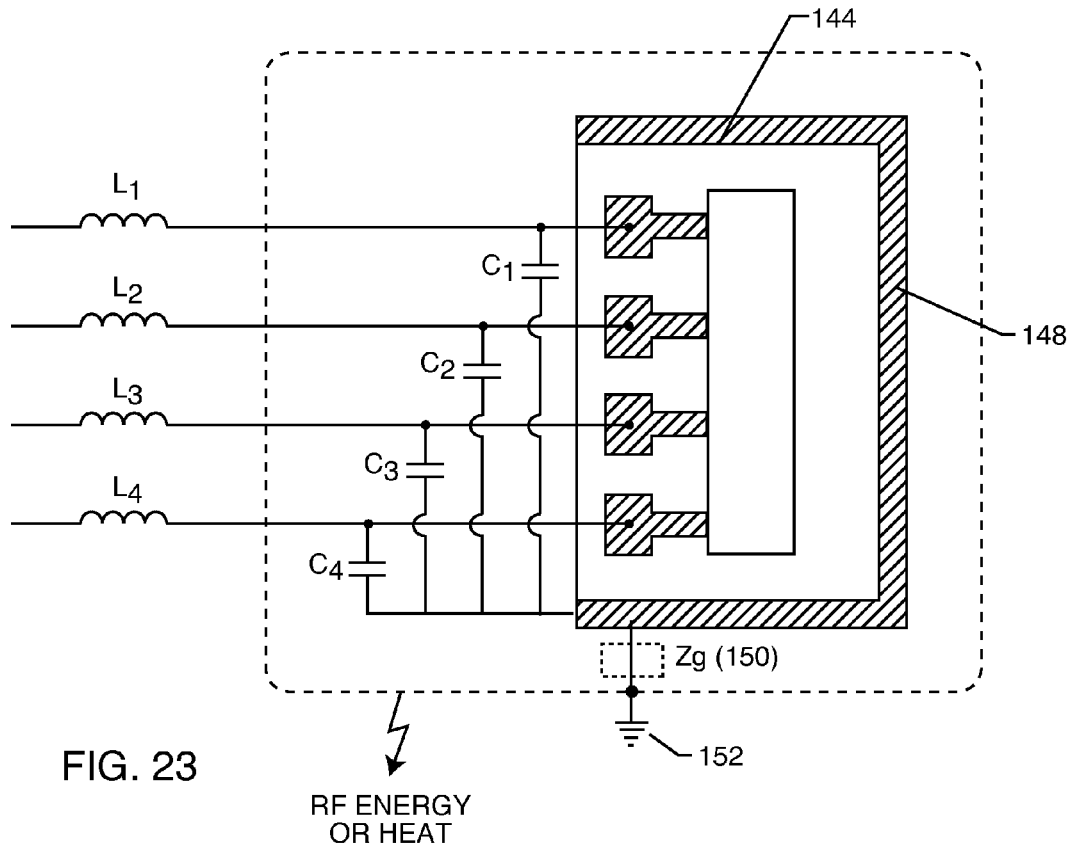
FIG. 23 is a schematic illustration showing the L-C circuits of FIG. 22.

FIG. 23 is a schematic diagram of the embodiment shown in FIG. 22.

Figure 24:
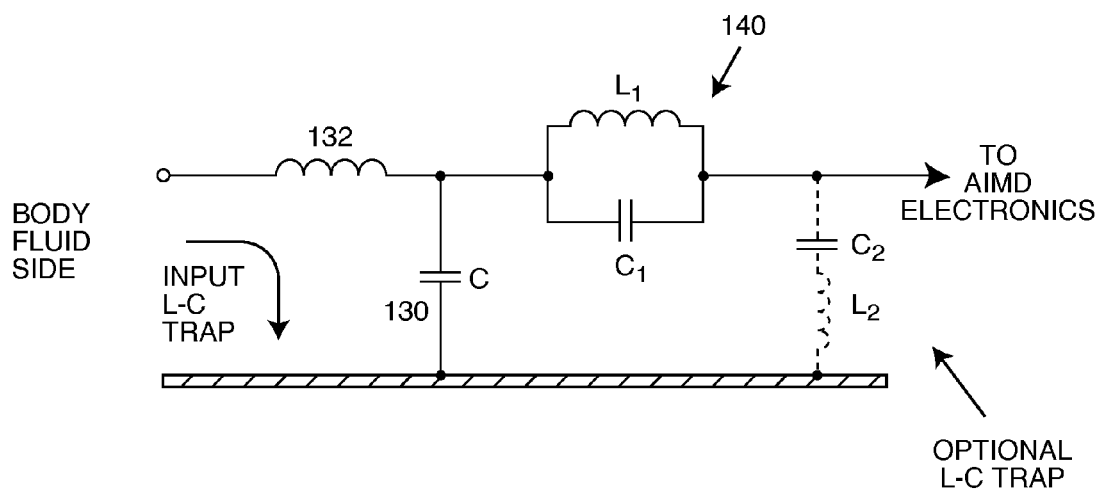
FIG. 24 is an electrical schematic diagram illustrating the basic circuit of FIG. 16, with a serial bandstop filter and an optional L-C trap disposed between an L-C filter of the present invention and the AIMD electronics.

FIG. 24 illustrates a dual L-C trap and low pass filter of the present invention consisting of inductor 132 and capacitor 130. In combination is a bandstop filter 140 consisting of inductor $L_1$ wired in parallel with capacitor $C_1$ which is designed to increase the attenuation of the overall filter at over a range of selected MRI frequencies. For example, inductor $L_1$ and capacitor $C_1$ could be designed to be resonant for the RF pulsed frequency of 1.5 Tesla MRI scanners. Also shown in dashed lines is an optional additional L-C trap filter consisting of capacitor $C_2$ and inductor $L_2$. This would also be tuned to be resonant at the MRI RF pulsed frequency. The purpose of FIG. 24 is to illustrate that the present invention consisting of novel L-C input traps and low pass filters can be combined with any number of series bandstop filters and additional L-C tank filters in order to improve performance. Series bandstop filters and additional L-C tank filters can also be combined with any of the low pass filters previously illustrated in FIG. 10.

From the foregoing, it will be appreciated that the dual function passive component network illustrated in its basic form in FIG. 16 comprises (1) an electromagnetically shielded AIMD housing 102, (2) at least one electronic sensing or therapy delivery circuit disposed within the AIMD housing (see reference voltage $V_3$), (3) a first conductive path having a series inductance L from the electronic circuit ($V_3$) to a tissue-stimulating or biological sensing electrode 124 at a distal end of the implanted lead 104, and (4) a second conductive path having a series capacitance C, capacitively coupled between the first conductive path and the AIMD housing 102. The capacitance C provides at least one component of an electromagnetic interference (EMI) filter for the electronic circuit. The inductance L and the capacitance C also form a frequency selective L-C trap for diverting high frequency energy induced on the first conductive path 104 at a selected frequency or range of frequencies to the AIMD housing 102 through the second conductive ground path. It will be noted that the second conductive path, which includes the series capacitance C, is coupled to the first conductive path between the inductor L and the electronic circuit ($V_3$). The inductor may comprise a circuit trace inductor, a flex cable inductance, or a chip inductor, and the capacitor may comprise a chip capacitor, a feedthrough capacitor, or a parasitic capacitance as illustrated.

Those skilled in the art will appreciate that the present invention can be extended to a number of other types of implantable medical devices, including deep brain stimulators, spinal cord stimulators, urinary incontinence stimulators and many other types of devices.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. An active implantable medical device (AIMD) comprising a dual function passive component input filter network, the active implantable medical device comprising:
   a) an electromagnetically shielded AIMD housing;
   b) at least one electronic sensing or therapy delivery circuit disposed within the AIMD housing;
   c) a first conductive path having a primary series inductance and extending from a first conductive path first end at the at least one electronic sensing or therapy delivery circuit to a first conductive path second end at a feedthrough connected to the AIMD housing, the feedthrough connectable to an implantable lead; and
   d) a second conductive path having a primary series capacitance and extending from a second conductive path first end connected anywhere along the first conductive path between the primary series inductance and the at least one electronic sensing or therapy delivery circuit to a second conductive path second end connected to the AIMD housing,
   e) wherein the primary series capacitance and the primary series inductance comprise an L-section broadband low pass electromagnetic interference (EMI) filter configured to protect the electronic sensing or therapy delivery circuit; and
   f) wherein the primary series inductance and the primary series capacitance also form a resonant L-C trap filter between the first conductive path second end to the second conductive path second end configured to divert RF energy induced at the feedthrough at the second end of the first conductive path to the AIMD housing.

2. The active implantable medical device of claim 1, wherein the resonant L-C trap filter has a circuit Q and a resulting 3 dB bandwid for diverting a range of MRI RF pulsed frequencies from the second end of the first conductive path at the feedthrough to the AIMD housing through the second conductive path.

3. The active implantable medical device of claim 2 wherein a center frequency of the range of MRI RF pulsed frequencies in megahertz is selected from the group of frequencies comprising the MRI constant times the static magnetic field strength in Teslas of an MRI scanner.

4. The active implantable medical device of claim 3, including a series resistance in at least one of the first and second conductive paths, wherein the resultant 3 dB bandwidth of the resonant L-C trap filter is selected from the group consisting on the order of tens of kilohertz, hundreds of kilohertz, and megahertz.

5. The active implantable medical device of claim 1, wherein the primary series inductance comprises an inductor or a plurality of inductors connected either in series or in parallel.

6. The active implantable medical device of claim 5, wherein the primary series capacitance comprises a capacitor or a plurality of capacitors connected either in series or in parallel.

7. The active implantable medical device of claim 6, wherein the capacitor comprises a feedthrough capacitor.

8. The active implantable medical device of claim 6 wherein the inductor or the plurality of inductors are disposed within the AIMD housing, or the capacitor or the plurality of capacitors are disposed within the AIMD housing.

9. The active implantable medical device of claim 1 wherein at least one secondary inductance is in series along the first conductive path between the at least one electronic sensing or therapy delivery circuit and the first end of the second conductive path, and wherein the primary series inductance, the primary series capacitance and the at least one secondary inductance also form a broadband T-section low pass filter configured to protect the at least one electronic sensing or therapy delivery circuit from electromagnetic interference.

10. The active implantable medical device of claim 9 wherein at least one secondary capacitance is added as a third conductive path connected at one end anywhere along the first conductive path between the at least one electronic sensing or therapy delivery circuit and the secondary inductance and connected at the other end to the AIMD housing, and wherein the primary series inductance, the primary series capacitance, the at least one secondary inductance and the at least one secondary capacitance form a broadband LL-section low pass filter configured to protect the at least one electronic sensing or therapy delivery circuit from electromagnetic interference.

11. The active implantable medical device of claim 10 wherein at least one additional inductor is added along the first conductive path or a plurality of additional inductors are added along the first conductive path with a plurality of capacitors added between the plurality of additional inductors and connected to the AIMD housing to form a broadband "n" element low pass filter configured to protect the at least one electronic sensing or therapy delivery circuit from electromagnetic interference.

12. The active implantable medical device of claim 1 being selected from the group consisting of an implantable hearing device, a neurostimulator, a brain stimulator, a cardiac pacemaker, a left ventricular assist device, an artificial heart, a drug pump, a bone growth stimulator, a urinary incontinence device, a spinal cord stimulator, an anti-tremor stimulator, an implantable cardioverter defibrillator, a congestive heart failure device, and a cardio resynchronization therapy device.

13. The active implantable medical device of claim 1 wherein the primary series inductance is disposed exteriorly of the AIMD housing.

14. The active implantable medical device of claim 13, wherein the primary series inductance is disposed within a header block for the AIMD.

15. The active implantable medical device of claim 1 wherein the primary series inductance is provided by an inductor having external surfaces comprised. entirely of biocompatible and non-migratable materials.

16. The active implantable medical device of claim 1 wherein the at least one primary series inductance is selected from the group consisting of a chip inductor, a circuit trace, a toroidal inductor, and a solenoid inductor.

17. The active implantable medical device of claim 1 wherein the at least one primary series capacitance comprises at least one chip capacitor.

18. The active implantable medical device of claim 1 including a bandstop filter disposed in series along a length of the first conductive path between a junction of the primary series inductance and the primary series capacitance and to the at least one electronic sensing or therapy delivery circuit, wherein the bandstop filter comprises a bandstop filter inductance in parallel with a bandstop filter capacitance.

19. An active implantable medical device (AIMD), comprising:
   a) a conductive device housing for the medical device, wherein the device housing provides an energy dissipating surface as a first node;
   b) at least one electronic sensing or therapy delivery circuit connected along a conductipath to a second node disposed within the device housing;
   c) a third node at or near a device feedthrough terminal or ferrule disposed in the device housing, wherein an electrical pathway passes through the device feedthrough terminal or ferrule in non-conductive relation to the device housing or the ferrule wherein the third node is connectable to an electrode configured for tissue-stimulating or biological-sensing;

d) a first inductance disposed between the second and third nodes; and e) first capacitance disposed between the first and second nodes, f) wherein the first inductance and the first capacitance form an L-section broadband low pass electromagnetic interference (EMI) filter for protecting the at least one electronic sensing or therapy delivery circuit; and g) wherein the first inductance and the first capacitance also form a resonant L-C trap filter between the third node and the first node for diverting RF energy induced at the third node to the device housing.

20. The active implantable medical device of claim 19 wherein the resonant L-C trap filter has a circuit Q and a resulting 3 dB bandwidth for diverting a range of MRI RE pulsed frequencies from an implantable lead connected to the third node to the first node at the device housing.

21. The active implantable medical device of claim 20 wherein a center frequency of the range of MRI RF pulsed frequencies in megahertz is selected from the group of frequencies comprising the MRI constant times the static magnetic field strength in Teslas of an MRI scanner.

22. The active implantable medical. device of claim 20 including a fourth node located along the conductive path between the second node and the at least one electronic sensing or therapy delivery circuit, and including a second inductance in series along the conductive path between the second and fourth node, and wherein the first inductance, the first capacitance and the second inductance also form a broadband T-section low pass filter that protects the at least one electronic sensing or therapy delivery circuit from electromagnetic interference.

23. The active implantable medical device of claim 22 including a second capacitance between the fourth node and the first node, wherein the first inductance, the first capacitance, the second inductance and the second capacitance also form a broadband LL-section low pass filter that protects the at least one electronic sensing or therapy delivering circuit from electromagnetic interference.

24. The active implantable medical device of claim 23 including an fifth node along the conductive path between the fourth node and the at least one electronic sensing or therapy delivery circuit, and including a third inductance between the fourth node and the fifth node, wherein the first inductance, the first capacitance, the second inductance, the second capacitance and the third inductance also form a broadband five-element low pass filter that protects the at least one electronic sensing or therapy delivery circuit from electromagnetic interference.

25. The active implantable medical device of claim 23 including an n node disposed between the fourth node and the at least one electronic sensing or therapy delivery circuit, and including an n inductance disposed between the n node and the fourth node and an n capacitance connected between the n node and the first node, wherein n can be any number, and wherein the first inductance, the first capacitance, the second inductance, the second capacitance, the n inductance and the n capacitance also form a broadband n-element low pass filter that protects the at least one electronic sensing or therapy deliver circuit from electromagnetic interference.

26. The active implantable medical device of claim 19 wherein the first inductance comprises an inductor or a plurality of inductors connected in series or in parallel.

27. The active implantable medical device of claim 26 wherein the first capacitance comprises a capacitor or a plurality of capacitors connected in series or in parallel.

28. The active implantable medical device of claim 27 wherein any of the capacitances or capacitors comprises at least one chip capacitor or feedthrough capacitor or feedthrough capacitor.

29. The active implantable medical device of claim 26 wherein any of the inductances or inductors are selected from the group consisting of a chip inductor, a circuit trace, a toroidal inductor, and a solenoid inductor.

30. The active implantable medical device of claim 19 being selected from the group consisting of an implantable hearing device, a neurostimulator, a brain stimulator, a cardiac pacemaker, a left ventricular assist device, an artificial heart, a drug pump, a bone growth stimulator, a urinary incontinence device, a spinal cord stimulator, an anti-tremor stimulator, an implantable cardioverter defibrillator, a congestive heart failure device, and a cardio resynchronization therapy device.

31. The active implantable medical device of claim 19 wherein the device feedthrough terminal comprises a hermetic device feedthrough terminal.

32. The active implantable medical device of claim 19 wherein the first inductance is disposed exteriorly of the device housing.

33. The active implantable medical device of claim 19 wherein the first inductance is disposed within a header block attached to the AIMD and the first capacitance is a feedthrough capacitor.

34. The active implantable medical device of claim 19 wherein the first inductance is provided by an inductor having external surfaces comprised entirely of biocompatible and non-migratable materials.

35. The active implantable medical device of claim 19 wherein the first inductance and the first capacitance are disposed within the device housing.

36. The active implantable medical device of claim 19, including a bandstop filter disposed along the conductive path between the second node and the at least one electronic sensing or therapy delivery circuit.

37. The active implantable medical device of claim 36 wherein the bandstop filter comprises a bandstop filter inductance in parallel with a bandstop filter capacitance.

* * * * *

UNITED STATES PATENT AND TRADEMARK OFFICE
CERTIFICATE OF CORRECTION

PATENT NO. : 8,483,840 B2  
APPLICATION NO. : 12/891587  
DATED : July 9, 2013  
INVENTOR(S) : Stevenson Page 1 of 1

It is certified that error appears in the above-identified patent and that said Letters Patent is hereby corrected as shown below:

In the Claims

Column 19, line 34, Claim 2, delete "bandwid" and insert --bandwidth--

Column 20, line 42, Claim 15, delete the "." after the word "comprised"

Column 20, line 64, Claim 19, delete "conductipath" and insert --conductive path--

Column 21, line 8, Claim 19, before the words "first capacitance" insert --a--

Column 21, line 20, Claim 20, delete "RE" and insert --RF--

Column 21, line 28, Claim 22, delete the "." after the word "medical"

Column 22, line 8, Claim 25, delete "deliver" and insert --delivery--

Column 22, line 18, Claim 28, after the words "chip capacitor" delete the words "or feedthrough capacitor"

Signed and Sealed this  
Third Day of June, 2014

Michelle K. Lee  
*Deputy Director of the United States Patent and Trademark Office*